(12) United States Patent
Irving et al.

(10) Patent No.: US 11,334,999 B2
(45) Date of Patent: May 17, 2022

(54) METHOD AND APPARATUS FOR IMAGING AN ORGAN

(71) Applicant: Perspectum Diagnostics Limited, Oxford (GB)

(72) Inventors: Benjamin J Irving, Oxford (GB); Chloe Hutton, Oxford (GB); Brady Michael John, Oxford (GB)

(73) Assignee: Perspectum Limited, Oxford (GB)

( * ) Notice: Subject to any disclaimer, the term of this patent is extended or adjusted under 35 U.S.C. 154(b) by 177 days.

(21) Appl. No.: 16/756,274

(22) PCT Filed: Oct. 12, 2018

(86) PCT No.: PCT/EP2018/077957
§ 371 (c)(1),
(2) Date: Apr. 15, 2020

(87) PCT Pub. No.: WO2019/076775
PCT Pub. Date: Apr. 25, 2019

(65) Prior Publication Data
US 2020/0334817 A1    Oct. 22, 2020

(30) Foreign Application Priority Data
Oct. 17, 2017    (GB) ...................................... 1717026

(51) Int. Cl.
*G06T 7/00* (2017.01)
*G06T 7/11* (2017.01)
*G06T 3/00* (2006.01)

(52) U.S. Cl.
CPC .......... *G06T 7/0016* (2013.01); *G06T 3/0068* (2013.01); *G06T 7/11* (2017.01); *G06T 7/97* (2017.01); *G06T 2207/10072* (2013.01)

(58) Field of Classification Search
CPC ........ A61K 31/451; A61P 25/08; A61P 25/28; C07D 211/24; C07D 211/42;
(Continued)

(56) References Cited

U.S. PATENT DOCUMENTS

| 7,343,195 B2 | 3/2008 | Strommer et al. |
| 10,149,744 B2 * | 12/2018 | Lior ......................... G06T 17/00 |

(Continued)

FOREIGN PATENT DOCUMENTS

WO    2014155299 A1    10/2014

OTHER PUBLICATIONS

Irving, Benjamin. "maskSLIC: regional superpixel generation with application to local pathology characterisation in medical images." arXiv preprint arXiv:1606. 09518 (2016) , pp. 1-7. Retrieved from the Internet: https://arxiv.org/pdf/1606.09518.pdf.

*Primary Examiner* — Bobbak Safaipour
(74) *Attorney, Agent, or Firm* — Optimus Patents US, LLC

(57) ABSTRACT

A method of quantifying changes in a visceral organ comprises acquiring first (310) and second (410) medical scans of a visceral organ at first and second timepoints. At least part of the visceral organ in the first medical scan is parcellated into a first set of one or more subregions (420), based on image content, each subregion comprising a plurality of voxels. The first medical scan (310) is aligned to the second medical scan (410), before or after parcellating the first medical scan (310). Then the second medical scan is parcellated into a second set of one or more subregions. A metric is evaluated for a subregion in the first medical scan (310), and for the corresponding subregion in the second medical scan (410). A difference in the metric values provides a measure of a change that has occurred in the subregion, between the first and second timepoints.

19 Claims, 16 Drawing Sheets

(58) Field of Classification Search
CPC ... C07D 211/52; A61B 2576/00; A61B 5/055; A61B 5/4842; G06T 2207/10072; G06T 2207/30016; G06T 2207/30048; G06T 2207/30056; G06T 2207/30061; G06T 2207/30084; G06T 3/0068; G06T 7/0016; G06T 7/10; G06T 7/11; G06T 7/97; G16H 30/40

See application file for complete search history.

(56) References Cited

U.S. PATENT DOCUMENTS

| | | | |
|---|---|---|---|
| 2001/0031920 A1 | 10/2001 | Kaufman et al. | |
| 2003/0053679 A1* | 3/2003 | Horn | G01B 11/005 |
| | | | 382/152 |
| 2008/0317310 A1 | 12/2008 | Suresh et al. | |
| 2013/0156280 A1* | 6/2013 | Kadir | G06T 7/0012 |
| | | | 382/128 |
| 2014/0126795 A1* | 5/2014 | Zhong | G01R 33/4828 |
| | | | 324/309 |
| 2014/0341452 A1 | 11/2014 | Kaftan et al. | |
| 2018/0259608 A1* | 9/2018 | Golden | G06N 3/02 |
| 2018/0279996 A1* | 10/2018 | Cox | A61B 8/483 |
| 2019/0012805 A1* | 1/2019 | Bertram | A61B 6/032 |
| 2019/0388188 A1* | 12/2019 | Kaza | A61C 7/002 |
| 2020/0043186 A1* | 2/2020 | Selviah | G06V 10/7515 |
| 2020/0320685 A1* | 10/2020 | Anssari Moin | G06V 10/26 |
| 2020/0333940 A1* | 10/2020 | Lee | G06F 3/017 |

* cited by examiner

300

400

500

METHOD AND APPARATUS FOR IMAGING AN ORGAN

FIELD OF THE INVENTION

This invention relates to the field of systems that are used to measure the human body.

BACKGROUND OF THE INVENTION

In the field of medical imaging, a variety of technologies can be used to investigate human anatomy. The following examples are types of scan that may be used to provide medical scans: X-Ray; Computed Tomography (CT); Ultrasound (US); Magnetic Resonance Imaging (MRI); Single Photon Emission Tomography (SPECT); and Positron Emission Tomography (PET). Each type of scan is referred to as an 'imaging modality'.

Medical scans provide a 'dataset'. A typical dataset comprises digital information about the value of a variable at each of many spatial locations. Most datasets provide digital information about locations in three-dimensional, '3-D', space. For example, CT scans may provide images of the chest of a patient, or of the head.

The smallest unit of a 3-D dataset for which there is data is a three-dimensional space that is termed a 'voxel'. A voxel may be considered analogous to a 3-D version of a 'pixel' in a two-dimensional image. A plane through a 3-D dataset is usually termed a 'slice'.

Where 3-D datasets are discussed below, the smallest unit of the dataset will be a voxel. Voxel size varies hugely across modalities and scan types. Where 2-D datasets are discussed below, such as X-Rays, then the smallest unit of the dataset will be a pixel. With 2-D datasets, a 2D slice acquired with LiverMultiscan™ may be 8 mm thick, with a spacing of 15 mm between successive slices. A typical pixel size might be 1 mm×1 mm.

The analysis of medical scans provides support to various branches of medicine. The recognition of structures and tissue types in medical scans is carried out by highly skilled staff. Such staff are typically either radiologists or trained operators of scanners. Radiologists may use medical scans as an input of information into the work of other clinical practitioners, for example those involved in making decisions about interventions that are necessary to help patients.

FIG. 1 illustrates a simplified example of visceral organs in a human body. Torso 110 of a human body is shown in plan view, for example when a scan has been carried out on a person who is lying down. The view in FIG. 1 is usually referred to as a 'coronal' view. Liver 120 and spleen 130 are visible in FIG. 1. Known MRI or CT scans can provide such views of whole organs.

FIG. 2 shows a method 200 that may be used in known systems.

An operator will usually select 210 an organ of interest. Then, depending on the information sought, the operator will select 220 a scanning mode. Scanning 230 with the selected scanning mode should then provide a suitable image of the one or more selected organs of interest. In some cases, an optional step may include a repeat scan 240 of the same one or more selected organs of interest. The operator may make a decision to carry out a repeat scan based, for example, on a decision to look for global changes in an organ.

A biological organ can be divided into contiguous sub-regions for local analysis, see reference [1] at the end of this 'Background' section. Various other methods such as 'clustering' are available to assess regions of a tumour or organs. Changes in a global description of an organ over time may help clinicians to recognise longitudinal progression of disease [2]. In brain imaging, the shape change of specific anatomical regions can be monitored over time [3]. Changes of the overall organ shape can be monitored [4]. These methods can only provide global descriptions of a region of interest.

In the remainder of this description, a visceral organ will be taken to mean an organ of the chest or abdomen. Examples of visceral organs are the liver, pancreas, spleen or kidneys.

[1] Irving et al. 2016. mask SLIC: Regional Superpixel Generation with Application to Local Pathology Characterisation in Medical scans. arXiv:1606.09518.

[2] O'Connor et al. 2016. Imaging Intratumor Heterogeneity: Role in Therapy Response, Resistance, and Clinical Outcome.

[3] Raz et al. 2005. Regional Brain Changes in Ageing healthy Adults: General Trends, Individual Differences and Modifiers.

[4] Heimann and Meinzer. 2009. Statistical shape models for 3D medical scan segmentation: A review.

SUMMARY OF THE INVENTION

According to a first aspect of the present invention, there is provided a method in accordance with appended claim 1. According to a second aspect of the present invention, there is provided a method in accordance with appended claim 2. According to a third aspect of the present invention, there is provided a medical scanning system in accordance with appended claim 18. According to a fourth aspect of the present invention, there is provided a non-transitory computer program product in accordance with appended claim 19. The dependent claims provide details of optional embodiments.

These and other aspects of the invention will be apparent from, and elucidated with reference to, the embodiments described hereinafter.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE PREFERRED EMBODIMENTS

Figure 1:
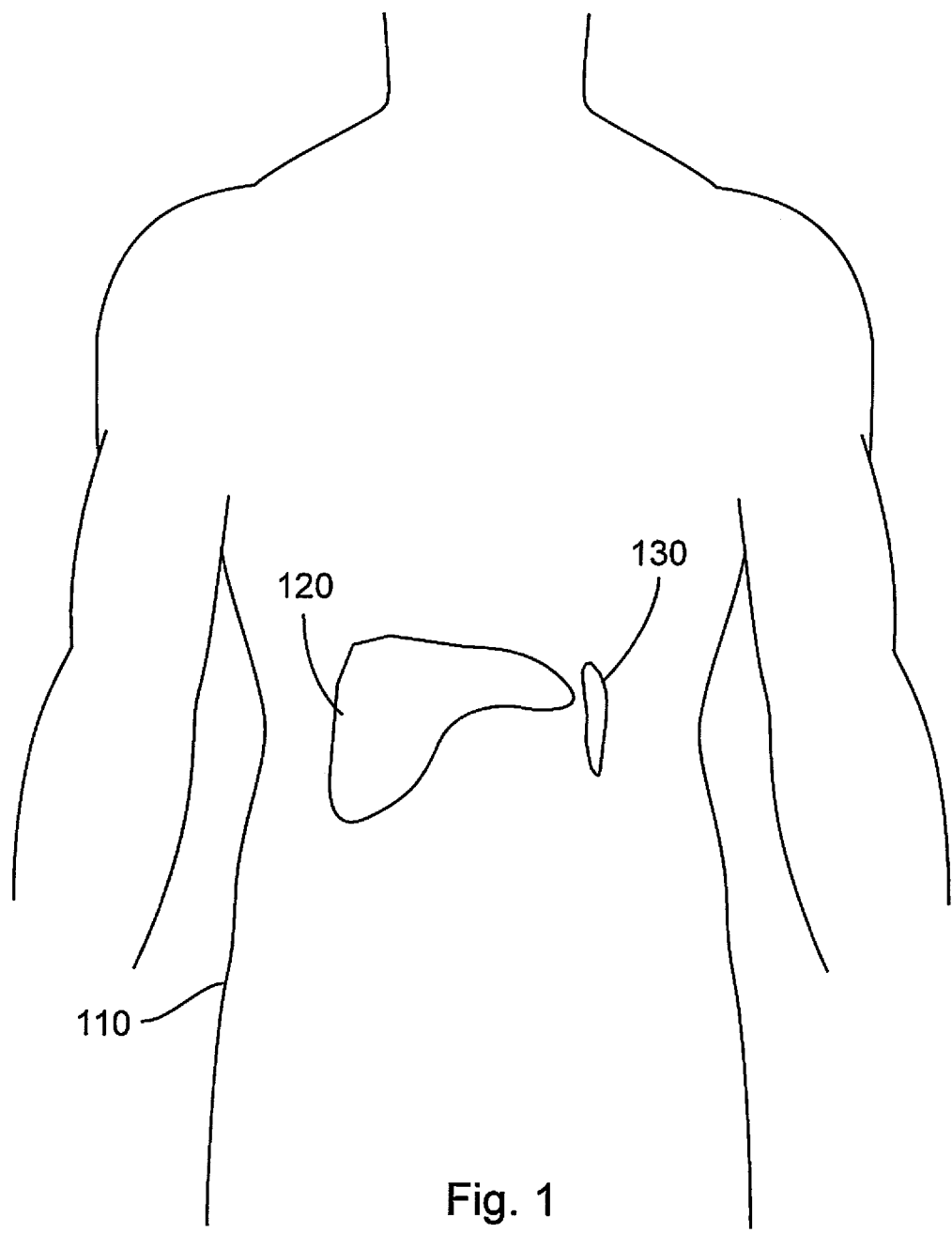
FIG. 1 illustrates a simplified example of visceral organs in a human body.
Figure 2:
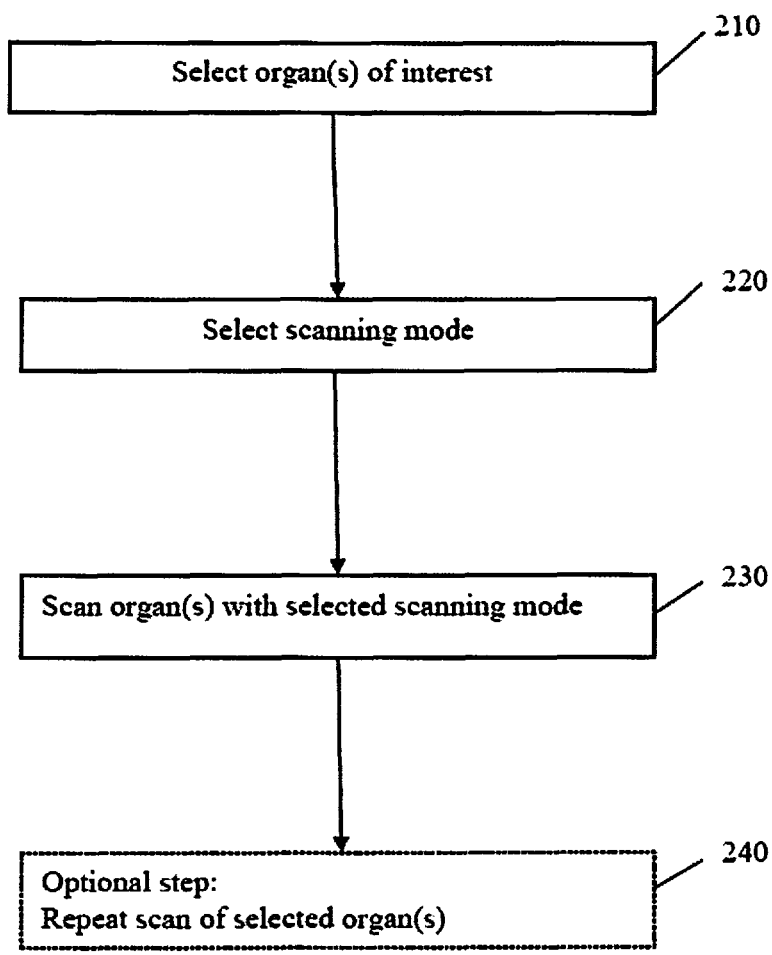
FIG. 2 illustrates a simplified flowchart of an example of a prior art method.

The present invention provides a method and apparatus for quantifying changes in a visceral organ of a human subject.

In accordance with a first aspect of the invention, a method of quantifying changes in a visceral organ of a human subject comprises acquiring a first medical scan at a first timepoint. The first medical scan is part of a first dataset and comprises a first set of voxels. The first medical scan comprises a first image of a visceral organ. The method also comprises acquiring a second medical scan at a second timepoint, the second medical scan being part of a second dataset and comprising a second set of voxels. The second medical scan comprises a second image of the visceral organ. The second timepoint may be before or after the first timepoint. At least part of the first image of the visceral organ in the first medical scan is parcellated into a first set of subregions based on image content, each subregion of the first set of subregions being defined by a regional representation comprising a plurality of voxels of the first set of voxels. Each subregion of the first set of subregions is non-overlapping with other subregions of the first set of subregions. The first medical scan is aligned to the second medical scan, before or after parcellating the first image of the visceral organ.

The method also comprises parcellating at least part of the second image of the visceral organ into a second set of subregions. Each subregion of the second set of subregions is defined by a regional representation comprising a plurality of voxels of the second set of voxels, and is non-overlapping with other subregions of the second set of subregions. Parcellating at least part of the second image of the visceral organ is based on the first set of subregions.

The method further comprises evaluating a metric for a subregion in the first image of the visceral organ to provide a first value of the metric, and evaluating the metric for a corresponding subregion in the second image of the visceral organ to provide a second value of the metric. A difference is evaluated between the first value of the metric and the second value of the metric, thereby providing a measure of a change that has occurred in the subregion between the first timepoint and the second timepoint.

The inventors have recognised that the global evaluation of medical scans with known techniques may lead a person interpreting the medical scan to miss changes within the medical scan. For example, a large visceral organ such as a liver may undergo changes over time that result in: (i) Positive changes in one or several regions of the liver; and (ii) Negative changes in other regions of the same liver. However, any global measure taken over the whole liver may only show a small change, due to an 'averaging out' across the liver. The particular method of the invention described above may provide a measurement that yields precise information about different states of a visceral organ over time, based on datasets acquired with, for example, an MRI scanner.

In many visceral organs, abnormalities are local within just part of a visceral organ, and circumscribed. In such cases, any significant changes may be only local, and the scale of such changes may be such that it cannot be known or reasonably estimated in advance. The changes may, for example, relate to the extent of a local abnormality and/or to the severity of a disease, as judged from the abnormal local region. The inventors have derived a method to detect and to measure significant changes to both of these parameters. Known systems do not provide direct measures of how all local regions within an organ evolve over time. Thus, with known systems, local changes in an organ may all too often be missed in the overall descriptive statistics of describing the organ.

In accordance with a second aspect of the invention, a method of quantifying changes in a visceral organ of a human subject comprises acquiring a first medical scan at a first timepoint. The first medical scan is part of a first dataset and comprises a first set of voxels. The first medical scan comprises a first image of a visceral organ. The method also comprises acquiring a second medical scan at a second timepoint, the second medical scan being part of a second dataset and comprising a second set of voxels. The second medical scan comprises a second image of the visceral organ. The method comprises aligning the first medical scan and the second medical scan. The first image of the visceral organ and the second image of the visceral organ are then parcellated jointly, based on image content for at least part of the first image of the visceral organ and part of the second image of the visceral organ. Parcellating the first image of the visceral organ provides a first set of subregions. Each subregion of the first set of subregions is defined by a first regional representation comprising a plurality of voxels, and is non-overlapping with other subregions of the first set of subregions. Parcellating the second image of the visceral organ provides a second set of subregions. Each subregion of the second set of subregions is defined by a regional representation comprising a plurality of voxels, and is non-overlapping with other subregions of the second set of subregions. The first set of subregions and the second set of subregions correspond. The method further comprises evaluating a metric for a subregion in the first image of the visceral organ to provide a first value of the metric, and evaluating the metric for a corresponding subregion in the second image of the visceral organ to provide a second value of the metric. A difference is evaluated between the first value of the metric and the second value of the metric, thereby providing a measure of a change that has occurred in the subregion between the first timepoint and the second timepoint.

The method above, in accordance with the second aspect of the invention, differs from the method of the first aspect in the aligning of the first and second medical scans. In addition, parcellation of the first and second images is done jointly, rather than one images being parcellated based on subregions that have previously been derived for the other image in isolation.

Figure 3A:
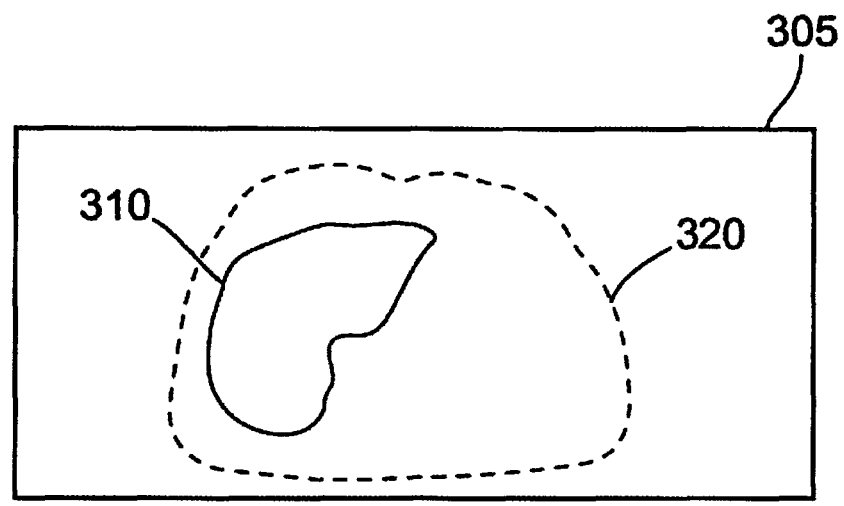
FIGS. 3A and 3B each illustrate an example of a slice of a medical scan from a dataset.

FIG. 3A illustrates an example of a first slice of a first medical scan from a first dataset.

In FIG. 3A, first slice 305 is a first medical scan. First slice 305 is one slice of a first dataset. The first dataset may be a 3-D volumetric image, and may comprise anywhere from 1-1000 slices such as first slice 305. First slice 305 has voxels as its most basic subunit. However, the first dataset may be any one of a 3D volumetric image, a stack of 2D images slices or a single 2D image slice.

The outline 320 of a torso of a human subject is visible in first slice 305. Within outline 320 is a first image 310 of a visceral organ. The visceral organ shown as the first image 310 might, for example, be a liver. Acquisition of the first image 310 is at a first timepoint, and first image 310 comprises a first set of voxels.

Figure 3B:
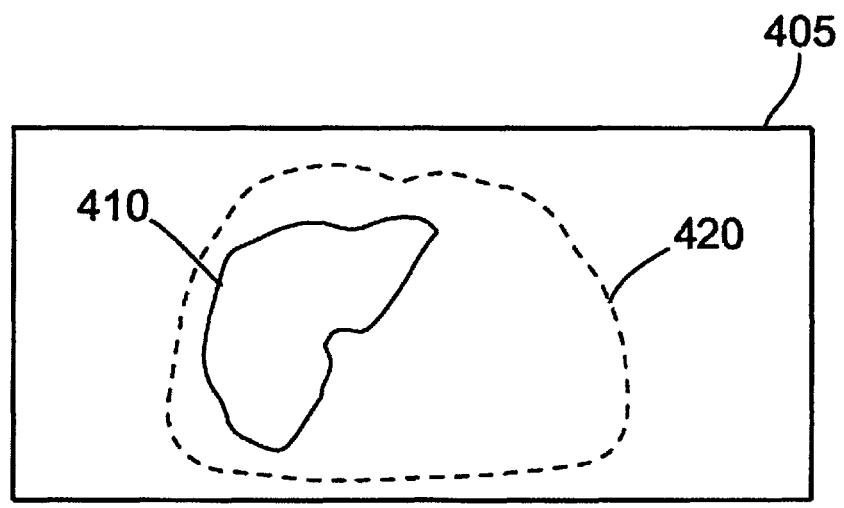

FIG. 3B illustrates at 300 an example of a slice of a second medical scan from a second dataset.

In FIG. 3B, second slice 405 is a second medical scan. Second slice 405 is one slice of a second dataset. The second dataset may be another 3-D volumetric image, and may also comprise anywhere from 1-1000 slices such as second slice 405. Second slice 405 has voxels as its most basic subunit. However, the second dataset may be any one of a 3D volumetric image, a stack of 2D image slices, or a single 2D image slice.

The outline 420 of a torso of a human subject is visible in second slice 405. Within outline 420 is a second image 410 of a visceral organ, which is an image of the same visceral organ as shown in FIG. 3A. Acquisition of second slice 405 with second image 410 is at a second timepoint, which may be before or after the first timepoint. Second image 410 comprises a second set of voxels.

The first time point and the second time point may be separated by sufficient time for the visceral organ to have undergone either a change in shape, or a change in the characteristics of at least one subregion. Typically, the first and second timepoints will be separated by at least a day, although separations as great as a year or several years are also possible. A change in shape may occur, for example, where an organ and/or surroundings parts of the body shown in the scan image have either lost or gained fat, for example over several months.

Figure 4:
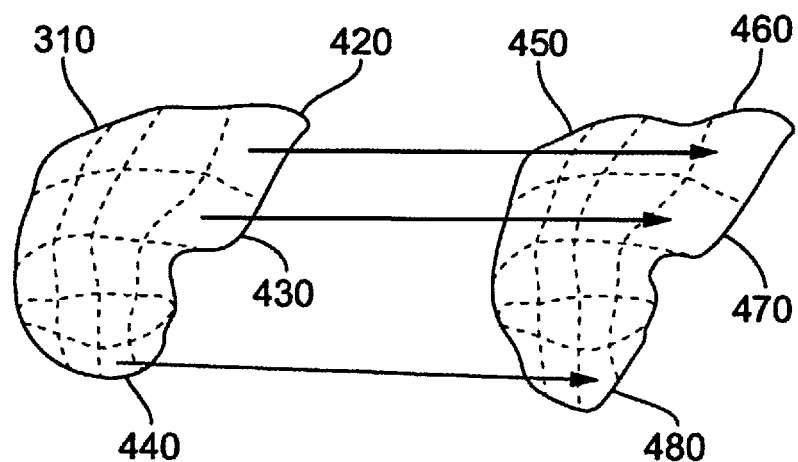
FIG. 4 illustrates an example of segmented, parcellated images in accordance with the invention.

FIG. 4 illustrates at 400 an example of segmented, parcellated images of the visceral organ in accordance with the invention.

FIG. 4 again shows the first image 310 of the visceral organ from FIG. 3A. First image 310 has been segmented from the remainder of first slice 305 shown in FIG. 3. The segmentation provides a first subset of the first set of image voxels of first image 310 that describe the visceral organ, but discards the remainder of the first set of image voxels of first slice 305.

Following segmentation, the first image 310 is then parcellated. Parcellation divides the first subset of image voxels into a plurality of subregions, which form a first set of subregions. First subregion 420, second subregion 430 and third subregion 440 are examples from the first set of subregions. The first set of subregions are 'non-overlapping', so that none of the subregions overlaps with any other subregion of the first set of subregions.

In FIG. 4, the whole of first image 310 has been parcellated. However, it is alternatively possible that only part of first image 310 will be parcellated.

Parcellation of first image 310 into the first set of subregions is based on the image content. The actual voxels values of the first subset of image voxels may be used to decide on the boundaries between subregions, so parcellation does not require a pre-defined model of the visceral organ or its internal structure. Although the actual voxel values are used in the calculation of the parcellations, there may also be a regularisation term to preserve spatial contiguity of the parcellations.

Thus a particular subregion of the first set of subregions generally has voxels of similar values across the subregion. So, for example, the voxels across first subregion 420 would typically have similar values. Often, therefore, the boundaries between subregions do not coincide completely with anatomical structures within the visceral organ itself. This approaches contrasts to that of known techniques, such as Ref [3], in which the shape of a pre-defined anatomy within the brain is considered.

Also shown on FIG. 4 is the second image 410 of the visceral organ from FIG. 3B.

Second image 410 has been segmented from the remainder of second slice 405 shown in FIG. 3B. The segmentation provides a second subset of the second set of image voxels of second image 410 that describe the visceral organ, but discards the remainder of the second set of image voxels of second slice 405.

As can be seen from the comparison view in FIG. 4, the outline of the second image 410 differs in several aspects from the outline of the first image 310. See for example the upper edge of each of first image 310 and second image 410.

As illustrated in FIG. 4, the second image 410 has been parcellated. Parcellation divides the second subset of image voxels into a plurality of subregions, which provide a second set of subregions. First subregion 460, second subregion 470 and third subregion 480 are examples of the second set of subregions. The second set of subregions are 'non-overlapping', so that none of the subregions of the second set overlaps with any other subregion of the second set.

The visceral organ has undergone changes between the first time point and the second timepoint. However, it is generally recognisable from FIG. 4 that first subregion 460, second subregion 470 and third subregion 480 of second image 410 correspond respectively to first subregion 420, second subregion 430 and third subregion 440 of first image 310.

An alignment of second image 410 to first image 310 has been carried out. That alignment may occur before or after parcellation of first image 310. Parcellation of second image 410 is based on the first set of subregions, and occurs after parcellation of first image 310, in accordance with the first aspect of the invention described above. The alignment may be carried out by image registration. Image registration is a technique that is used in the interpretation of scan images to ensure that sections of a medical scan can be brought into positional correspondence with corresponding sections of another medical scan of the same object.

As an alternative, and in accordance with the second aspect of the invention described above, an alignment of the second image 410 to first image 310 may be performed before any parcellation. Then parcellation of first image 310 and second image 410 may be carried out together, jointly, based on the content of first image 310 and of second image 410. A decision about the shape and location of the boundaries of any subregion will be made on the basis of the image content at the relevant locations on both images. Parcellating at least part of the visceral organ, based on the image content, may comprise carrying out the parcellating based on intensities of the first set of voxels and/or intensities of the second set of voxels.

In FIG. 4, the whole of second image 410 has been parcellated. However, it is also possible that only part of second image 410 will be parcellated. Generally, at least as much of second image 410 as of first image 310 will be parcellated.

A comparison of first image 310 and second image 410 can provide valuable information about changes to the visceral organ between the first timepoint and the second timepoint. A metric is evaluated for at least one sub-region of the first set of subregions. The result of the evaluation is a first value of the metric for each of the at least one sub-region of the first set of subregions. The metric is then evaluated for the one or more corresponding sub-regions of the second set of subregions, to provide a second value of the metric for each of those subregions.

When the metric is evaluated for a plurality of sub-regions of the first set of subregions, the result will be a 'first value' for each subregion of the first image 310 of the visceral organ. Then the evaluation of the metric for the corresponding subregions of the second image 410 of the visceral organ will provide a 'second value', for each corresponding sub-region from the second set of subregions.

Valuable information about changes to the visceral organ can then be derived by evaluating, for each subregion, a difference between the first value of the metric and the second value of the metric. The difference value of the metric for each subregion thereby provides a measure of changes that have occurred in the subregion between the first timepoint and the second timepoint.

Table 1 below shows a non-limiting numerical example of the various parameters discussed above. The unit 'cT1' is the T1 relaxation time that would have been measured by the MRI scanner if the iron concentration in the patient liver was "normal"' Thus cT1 is sometimes referred to in this field as the 'iron-corrected T1 relaxation time'.

TABLE 1

Change in metric for six subregions over four scans

| Sub-region of image | Change in cT1 (ms) | | | |
|---|---|---|---|---|
| | From 1$^{st}$ to 2$^{nd}$ scan | From 1$^{st}$ to 3rd scan | From 1$^{st}$ to 4th scan | From 1$^{st}$ to 5th scan |
| 1 | −30 | −70 | −75 | −91 |
| 2 | −10 | −12 | −30 | −57 |
| 3 | −80 | −140 | −150 | −152 |
| 4 | 5 | 1 | 5 | 2 |
| 5 | −6 | −20 | −61 | −121 |
| 6 | −1 | −3 | 2 | 0 |

In Table 1, a first image 310 has six subregions after parcellation, see the left column of table 1. The subregions are numbered 1-6. The first column under the group heading 'Change in cT1 (ms)' shows the change in cT1 value for each subregion, between a first scan and a second, subsequent scan. The cT1 value is the voxel value from an initial image, i.e. the 1$^{st}$ scan. The cT1 value provides the base point from which changes in the visceral organ are to be measured.

Only for subregion 4 has the cT1 value increased. For subregions 1-3 and 5, the cT1 value has decreased. The values in the table allow easy recognition of the degree of change of cT1 for subregions 1-3, 5 and 6. The cT1 value has changed much more significantly for region 3 than for any of the other regions.

The columns under the heading 'Change in cT1 (ms)' show changes relative to the original scan that are detected at the timepoints of the second, third, fourth and fifth scans. Subregion 3 continued to show the greatest change in cT1 value. However, large changes in cT1 value for subregion 5 were apparent in the final two scans.

Table 1 shows clearly that the amount of change in each subregion varied greatly. That variation was both between different subregions, and was also between subsequent scans for some subregions. A prior art approach that provided a mean value of cT1 change for the whole organ would not have indicated any of the particular changes shown in Table 1.

Table 2 shows results for five different visceral organs. These organs might be in five different people. The entries in the table show the percentage volume of each organ that has shown an increase in the cT1 value that exceeds a threshold, and the percentage of each organ that has shown a decrease in the cT1 value that exceeds another threshold. The three columns in the centre of Table 2 provide data derived from four scans of each organ, at four different timepoints.

TABLE 2

Percentage of increase/decrease for five visceral organs

| Case/organ | Percentage increase or decrease of measured cT1 value for organ ('Inc' show % increase; 'Dec' shows % decrease) | | | |
|---|---|---|---|---|
| | From 1$^{st}$ to 2$^{nd}$ scan | From 1$^{st}$ to 3rd scan | From 1$^{st}$ to 4th scan | Comment |
| 1 | Inc: 11% | Inc: 41% | In: 50% | Strong increase; |
| | Dec: 5% | Dec: 0% | Dec: 0% | no subregions decrease |
| 2 | Inc: 34% | Inc: 68% | Inc: 70% | Very strong increase; |
| | Dec: 2% | Dec: 1% | Dec: 0% | no subregions decrease |
| 3 | Inc: 9% | Inc: 42% | Inc: 63% | Strong increase; |
| | Dec: 6% | Dec: 0% | Dec: 0% | no subregions decrease |
| 4 | Inc: 0% | Inc: 0% | Inc: 2% | Relatively constant |
| | Dec: 0% | Dec: 0% | Dec: 0% | |
| 5 | Inc: 15% | Inc: 23% | Inc: 28% | Medium proportion of |
| | Dec: 0% | Dec: 31% | Dec: 52% | subregions show increase; Large proportion of subregions show decrease. |

Organ 5 in row five of Row five of Table 2 shows a case where 28% of the organ shows an increase in cT1 value. However, 59% of the organ shows a decrease of cT1 value. Known systems that produce a mean cT1 value across the organ would not have shown a very significant change. However, with the invention, it is clear that more extreme changes in cT1 value in fact occurred in parts of the organ. It is also clear which parts of the organ have shown those changes, and how great the individual changes are.

Thus the invention allows quantitative estimates of changes in an organ. Such estimates are particularly valuable in organs that otherwise might show little change between successive scans, due to averaging out of changes in cT1 value across the whole organ. Radiologists may derive information such as that derived by the invention, and in turn pass it to other clinical practitioners, who may for example interpret a decrease in cT1 value as an improvement in condition of the visceral organ, and an increase in cT1 value as a deterioration.

Figure 5:
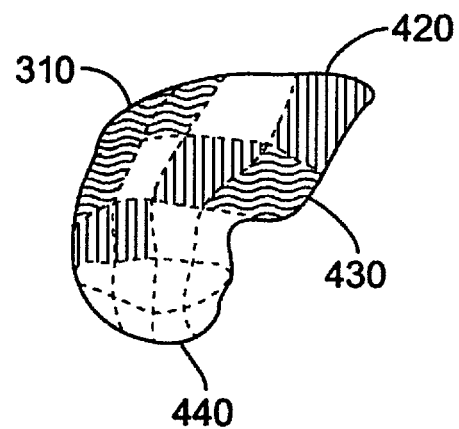
FIG. 5 illustrates an example of changes within the segmented, parcellated image of FIG. 4.

FIG. 5 illustrates at 500 an example of changes within the segmented, parcellated image of FIG. 4.

FIG. 5 shows the first image 310 once again. FIG. 5 also shows first subregion 420, second subregion 430 and third subregion 440, of the first set of subregions. Each of first subregion 420 and second subregion 430 has been marked with a different form of shading. The shading indicates a range of values for the difference between the first value of the metric and the second value of the metric. Although FIG. 5 shows the first image 310, the difference between the first value of the metric and the second value of the metric could alternatively be displayed as an overlay on the second image 410. If second image 410 is the more recent image, then such a display of second image 410 may be preferred.

If first subregion 420, second subregion 430 and third subregion 440 were respectively subregions 2, 3 and 4 in Table 1, and the second image 410 was the '$2^{nd}$ scan' referred to in the left column under the heading 'Change in cT1 (ms)', then the shading of first image 310 might for example be:

(i) Vertical shading, as shown in first subregion 420, for a cT1 change that lies between −20 and −50 milliseconds;

(ii) Horizontal waved shading, as shown in second subregion 430, for a cT1 change that lies between −50 and −100 milliseconds;

(iii) No shading, as shown in third subregion 440, when the change in cT1 is numerically positive, i.e. greater than zero milliseconds.

Figure 6:
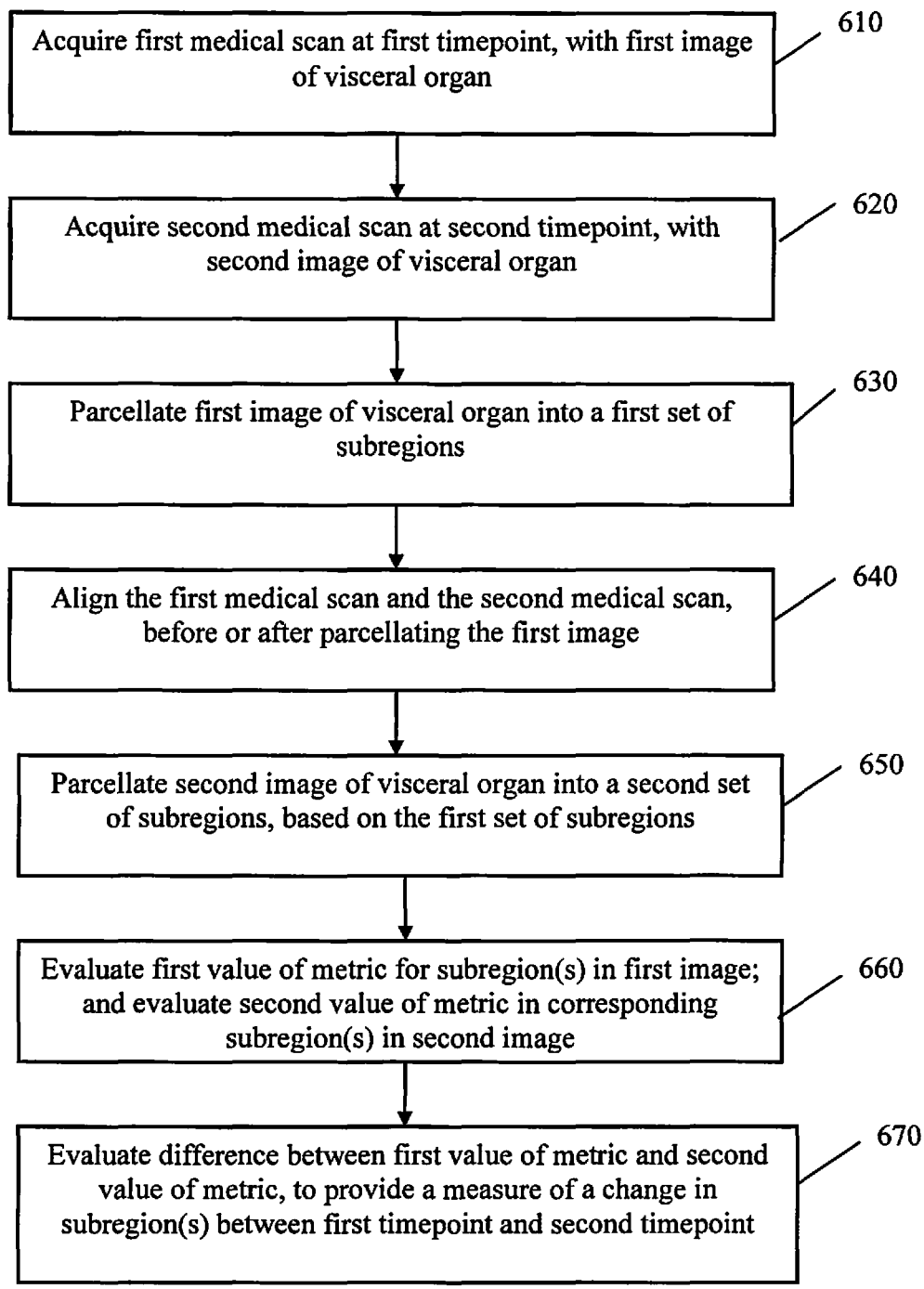
FIG. 6 is a simplified flowchart of a method in accordance with the invention.

FIG. 6 is a simplified flowchart of a method 600 in accordance with the first aspect of the invention.

At 610, the first medical scan is acquired at the first timepoint. At 620, the second medical scan 410 of the visceral organ is acquired at a second timepoint.

At 630, the first image 310 of the visceral organ is parcellated into a first set of subregions. At 640, the first medical scan 310 and the second medical scan 410 are aligned, which may be before or after parcellating 630 the first image 310. At 650, the second image 410 of the visceral organ is parcellated into a second set of subregions, based on the first set of subregions.

At 660, a first value of the metric is evaluated for subregion(s) in first image 310, and a second value of the metric is evaluated in corresponding subregion(s) in second image 410.

At 670, a difference between the first value of the metric and the second value of the metric is evaluated, to provide a measure of a change in one or more subregions between the first timepoint and the second timepoint.

The outcome of step 670 may be subject to a further threshold detection step. Such a further threshold detection step then provides information that is shown as the various shading shown in FIG. 5.

Figure 7:
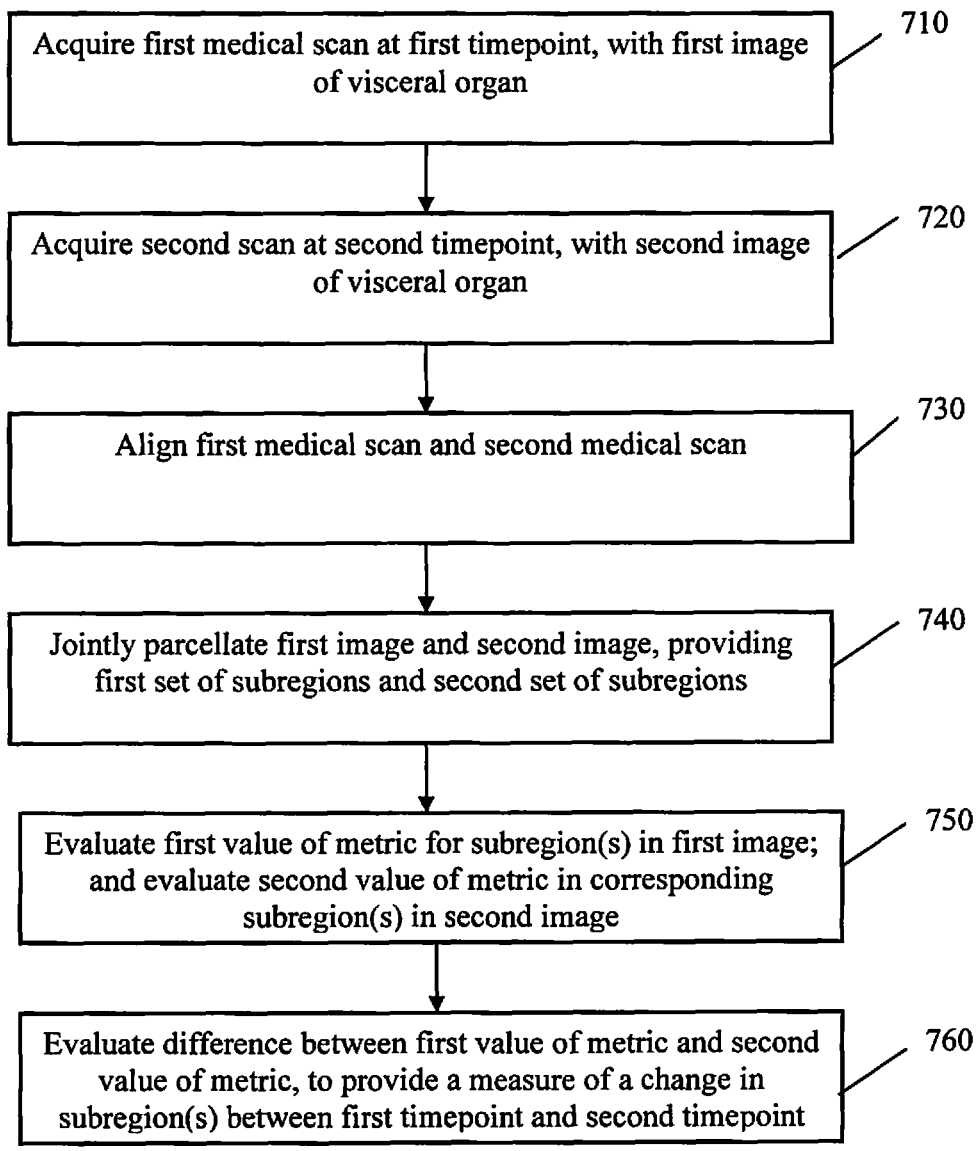
FIG. 7 is a simplified flowchart of another method in accordance with the invention.

FIG. 7 is a simplified flowchart of a method 700 in accordance with the second aspect of the invention.

At 710, the first medical scan is acquired at a first timepoint. At 720, the second medical scan is acquired at a second timepoint. At 730, the first medical scan and the second medical scan are aligned.

At 740, the first image 310 of the visceral organ and the second image 410 of the visceral organ are jointly parcellated, for example at the same time. Parcellation of the first image 310 provides a first set of subregions. Parcellation of the second image 410 provides a second set of subregions.

At 750, a first value of the metric is evaluated for subregion(s) in the first image 310, and a second value of the metric is evaluated in corresponding subregion(s) in the second image 410.

At 760, a difference between the first value of the metric and the second value of the metric is evaluated, to provide a measure of a change in one or more subregions between the first timepoint and the second timepoint.

The outcome of step 760 may be subject to a further threshold detection step. Such a further threshold detection step then provides information that is shown as the various shading shown in FIG. 5.

Scan and Image Acquisition; Alignment; and Parcellating

Various approaches are possible to the steps of acquiring the first medical scan with first image 310 and the second medical scan with second image 410. Various approaches are also possible to the parcellating and the aligning steps. The first medical scan and the second medical scan may be acquired using a Magnetic Resonance Imaging, MRI, scan. Each voxel of such scans then provides either: quantitative T1 values; quantitative T2* values; cT1 values that are based on T1 values using T2* as a correction; or Proton Density Fat Fraction, PDFF, values. Alternatively, a combination of T1, T2* and/or PDFF values may be provided. The difference between the first value of the metric and the second value of the metric is then a difference for any subregion in either: the T1 values; the T2* values; the cT1 values; or the PDFF values.

Parcellating the first image 310 of the visceral organ and/or in the second image 410 of the visceral organ may further comprise creating a piece-wise constant representation of the visceral organ, whereby each subregion is locally similar.

Parcellating the visceral organ in the first image 310 and/or in the second image 410 may comprise superpixel clustering, within the visceral organ, after segmenting.

Parcellating the visceral organ in the first image 310 and/or in the second image 410 may comprise creating a representation of local similarity within the visceral organ. Similarity is defined on the basis of either multiple imaging modalities, or texture.

Aligning the first and second medical scans may comprise aligning image content-derived information that defines subregions of the first image 310 of the visceral organ and the second image 410 of the visceral organ. However, aligning may comprise aligning image content-derived information that defines the visceral organ of the first image 310 and the second image 410. Alternatively, aligning may comprise using a transformation to explicitly align: points that lie on boundaries of subregion(s); and/or points that lie on a boundary of the visceral organ.

The Metric

The metric may be a summary statistic of spatial texture across at least one subregion. The metric may be evaluated for a plurality of subregions of the first image 310 of the visceral organ and for corresponding subregions of the second image 410 of the visceral organ.

The difference between the first value of the metric and the second value of the metric may be evaluated for each subregion, to thereby provide a plurality of difference values. Those difference values may be plotted. The plurality of difference values may be plotted on either a graph or on a spatial plot of the subregions. The graph or spatial plot provides a visual projection of changes in each subregion between the first timepoint and the second timepoint.

A threshold of change may be defined for the metric. In this case, the difference between the first value of the metric and the second value of the metric may be compared against the threshold of change for at least one subregion. This comparison thereby identifies whether the threshold of change has been exceeded for the at least one subregion. The first image 310 of the visceral organ or the second image 410 of the visceral organ can then be displayed with an overlay showing subregions for which the metric has exceeded the threshold of change.

In addition, the invention may comprise calculating a percentage of the visceral organ that has undergone a change that exceeds the threshold of change. The percentages of the visceral organ that have undergone a change that exceeds the threshold of change can then be plotted. The plot may be either a graph or a spatial plot of the subregions.

Although one metric has been described, the method may be repeated with other metrics. Other metrics may be applied to only some of the subregions to which the metric described above has been applied.

Third and Further Medical Scans

For simplicity of explanation, the detailed embodiments in FIGS. 3A, 3B, 4 and 5 above have been restricted to a discussion of only two medical scans. However, the invention is envisaged as applying to more than two medical scans. The inventors have realised that changes in a given region of a visceral organ may occur in very different ways, over different time periods. For example, a given region of the visceral organ may show an increase in cT1 value between two or more successive scans, but then show a decrease between a further two or more successive scans.

With known systems, it may be hard or impossible to recognise such localised change in a visceral organ. This is particularly the case when the direction of changes, i.e. increasing or decreasing cT1 value in milliseconds, varies between various ones of a series of medical scans. Here the medical scans, i.e. the datasets, may sometimes be acquired over periods of several years. The available medical scans may also comprise a wide variety of e.g. MRI scans, CT scans and 2-D X-Rays.

In some circumstances, a medical scan may comprise a single 2-D slice such as a single MRI slice acquired for a particular portion of a visceral organ that is being followed, after evaluation of earlier medical scans that show that particular portion of the visceral organ. In one typical scenario, a human patient may be breathing and hence moving during a medical scan. Thus a single 2-D slice may be acquired with an MRI at a particular, precise time. That time may be, for example, when an operator of the scanner considers movement to be at a minimum, such as after or before exhalation.

Thus the invention may acquire at least a third medical scan at a third timepoint. The third medical scan will provide a third image of the visceral organ. The method of the first or second aspect of the invention, i.e. claim 1 or 2, may then be repeated with the third medical scan and the third image of the visceral organ. With the first aspect of the invention, the metric for the third and subsequent images may be evaluated in comparison to the first image. With the second aspect of the invention, parcellation may take account of three or more images, when deriving the subregions. Essentially, the method steps of claim 1 or claim 2 are repeated using the third medical scan comprising the third image of the visceral organ, and at least one of the first medical scan and the second medical scan.

Difference values for the metric between the first, second and third images of the visceral organ can be plotted. The plot may be either a graph or a spatial plot. Such a plot provides a visual projection of changes that have occurred in subregions between the first, second and third timepoints.

When three or more medical scans are available, a threshold of change can again be defined for subregions of the images of the visceral organ. Then differences between the first, second and third values of the metric can be compared against the threshold of change for the subregions. This comparison identifies whether the threshold of change has been exceeded for the subregions. A percentage of the visceral organ that has undergone a change that exceeds the threshold of change can be calculated, for the images in the second and/or third medical scans. Then a plot can be made for the second and/or third images. The plot can show percentages of the visceral organ that have undergone the change that exceeds the threshold of change.

Methods of Detailed Embodiments

Figure 8:
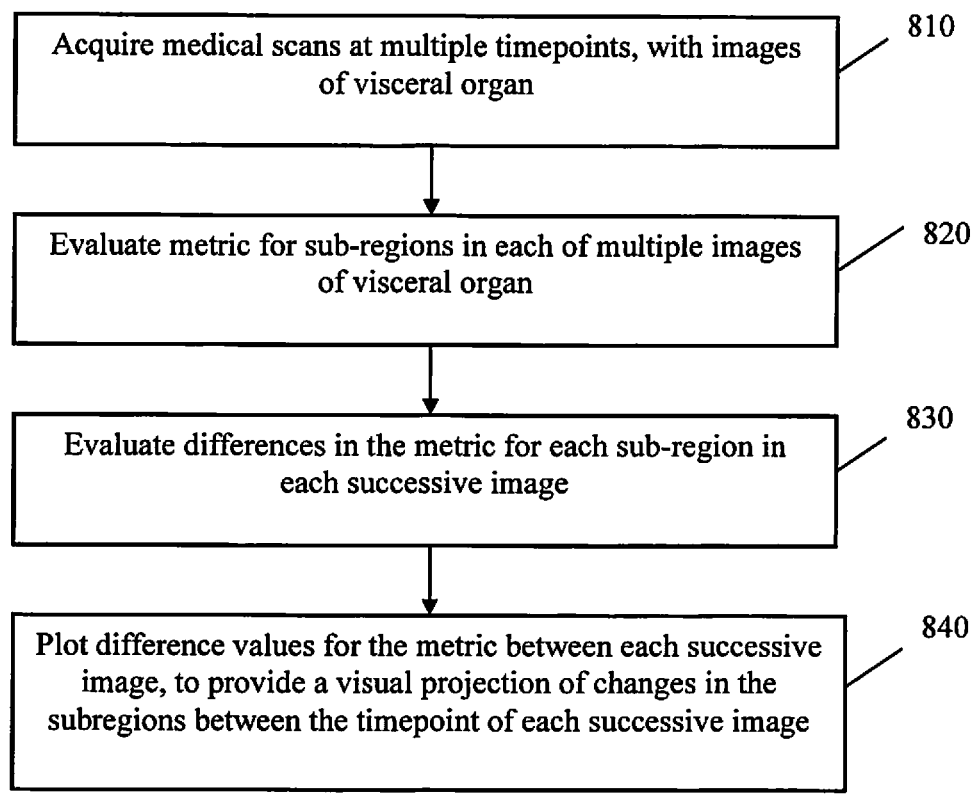
FIG. 8 is a simplified flowchart of a method in accordance with an embodiment.

FIG. 8 is a simplified flowchart of a method 800 in accordance with an embodiment. Method 800 of FIG. 8 provides a detailed embodiment of difference calculation for three or more medical scans taken at different timepoints.

At 810, medical scans of a visceral organ are acquired at multiple timepoints. The medical scans will be acquired as part of datasets as described previously. The images of the visceral organ in those medical scans are then parcellated using the alignment and parcellation described earlier with reference to either method 600 or method 700.

At 820, the metric is evaluated for multiple sub-regions in each image of the visceral organ. Step 820 corresponds to step 660 or step 750, but for the images of the visceral organ in the three or more medical scans taken in step 810.

At 830, the difference in the metric is evaluated for each sub-region in each successive image of the visceral organ. If there are, for example, six scans, then it is possible to evaluate the difference between the image of the visceral organ in each of the second to sixth scans, starting from values of the metric for subregions of the first image of the visceral organ. Each row of table 2 above shows four scans for each organ. There are therefore three difference values for each image of the visceral organ, in each row of table 2.

At 840, the difference values for the metric are plotted between each successive image of the visceral organ, to provide a visual projection of changes in the subregions between the timepoints of each successive medical scan. So, starting for example from the values in table 2, a two-dimensional plot could be created for each organ, showing the changes in the metric from the $1^{st}$ to $2^{nd}$, from the $1^{st}$ to $3^{rd}$, and from the $1^{st}$ to $4^{th}$ scans.

Figure 9:
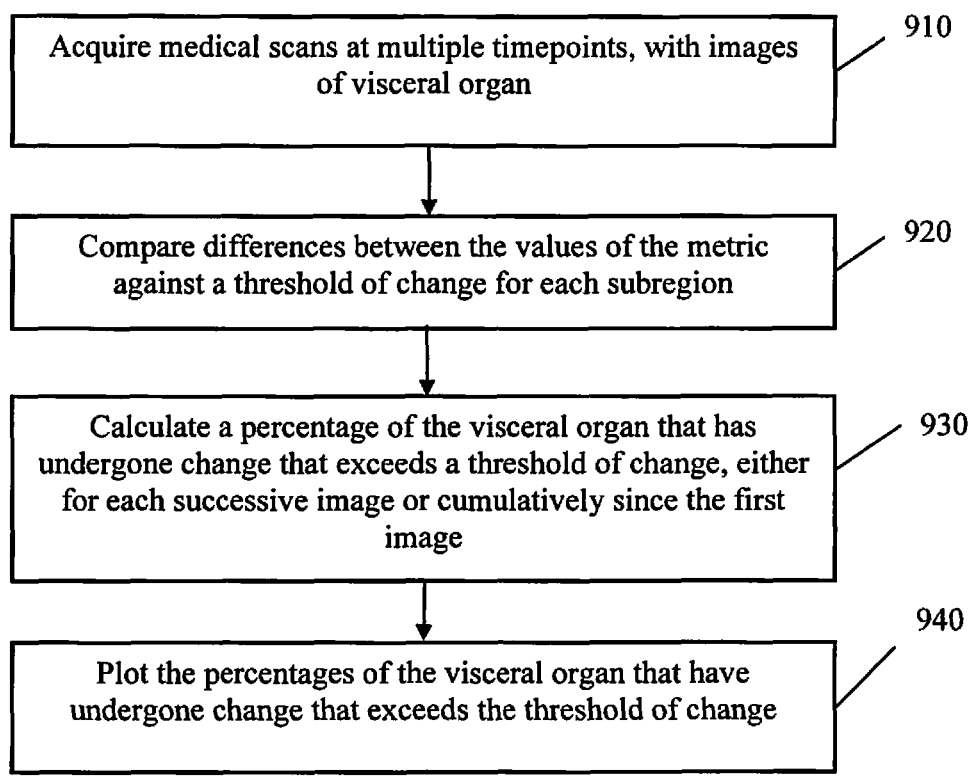
FIG. 9 is a simplified flowchart of a method in accordance with another embodiment.

FIG. 9 is a simplified flowchart of a method 900 in accordance with another embodiment. Method 900 of FIG. 9 provides a detailed embodiment of a method of deriving the percentages of a visceral organ that have undergone a change that exceeds a threshold, for multiple medical scans.

At 910, medical scans of a visceral organ are acquired at multiple timepoints. The medical scans will be acquired as part of datasets as described previously. The images of the visceral organ in the medical scans are then parcellated, using the alignment and parcellation described earlier with reference to either method 600 or method 700. Values of the metric are then obtained for each subregion of interest in each image of the visceral organ, see again steps 660, 750 and 820.

At 920, the differences between the values of the metric are compared against a threshold of change, for each subregion. At 930, a percentage of the visceral organ that has undergone change exceeding a threshold of change is calculated. That calculation may be performed either for each successive image of the visceral organ, or cumulatively since the first image of the visceral organ. Step 920 could, for example, be applied to the entries in table 1 above.

At 940, a plot is made of the percentages of the visceral organ that have undergone change that exceeds the threshold of change.

An Alternative Approach to Alignment and Parcellation

The methods of the first and second aspects of the invention have been described above and in claims 1 and 2, and illustrated in flowchart form in FIGS. 6 and 7. However, the inventors have envisaged a third alternative approach to the alignment and parcellation steps, which third approach involves replacing some steps of the first and second aspects of the invention. The third approach is not claimed, but is described in the following paragraph for completeness.

In the third approach to the alignment and parcellation, the alignment comprises aligning the first medical scan and the second medical scan, after having parcellated both the first image 310 of the visceral organ and the second image 410 of the visceral organ. Then a correspondence is created between the first set of subregions and the second set of subregions. With this third approach, the first image 310 and second image 410 can be parcellated entirely separately, in contrast to the joint parcellation of the method of the second aspect of the invention. In order to be able to calculate the metric, the correspondence allows metric values to be compared for subregions in the first image 310 and corresponding subregions in the second image 410.

Examples of Applications of the Invention

Figure 10:
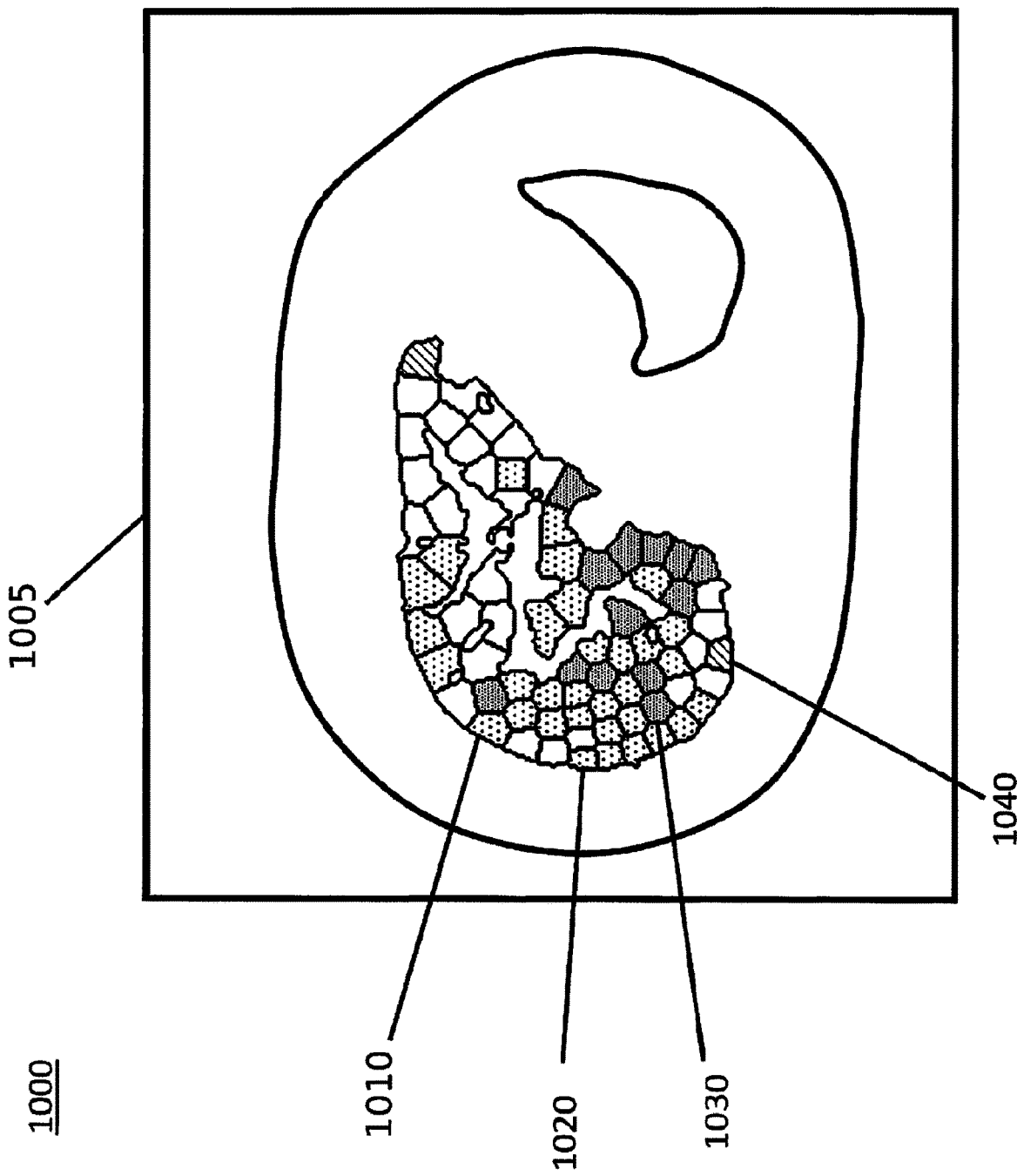
FIG. 10 is an example of a slice of a three dimensional medical scan taken from an MRI scan dataset.

FIG. 10 is an example of a slice of a three dimensional medical scan taken from an MRI scan dataset.

Shown at 1000 is a single slice 1005 from a dataset is shown in FIG. 10. Image 1010 of a visceral organ is shown by the dark outline around an irregular region at the left centre of FIG. 10. Image 1010 has been segmented from the remainder of slice 1005. Image 1010 in fact shows a liver parenchyma.

Within image 1010, first subregion 1020, second subregion 1030 and third subregion 1040 are shown as examples. The darkness of all the subregions within the perimeter of image 1010 corresponds to values on the scale at the right of FIG. 10. The scale shows change in cT1 values in milliseconds. The values shown may be the change in cT1 values between just two medical scan images, such as first medical scan image 310 and second medical scan image 410 discussed in relation with FIGS. 3-7. However, values shown may be the change in cT1 values between any two of a series of three or more medical scan images, as discussed in relation with FIGS. 8 and 9. In some cases, with three or more medical images, the most valuable plot might be a plot showing the difference in cT1 value between the first image and an intermediate image, rather than simply between the first and last of the images.

Figure 11:
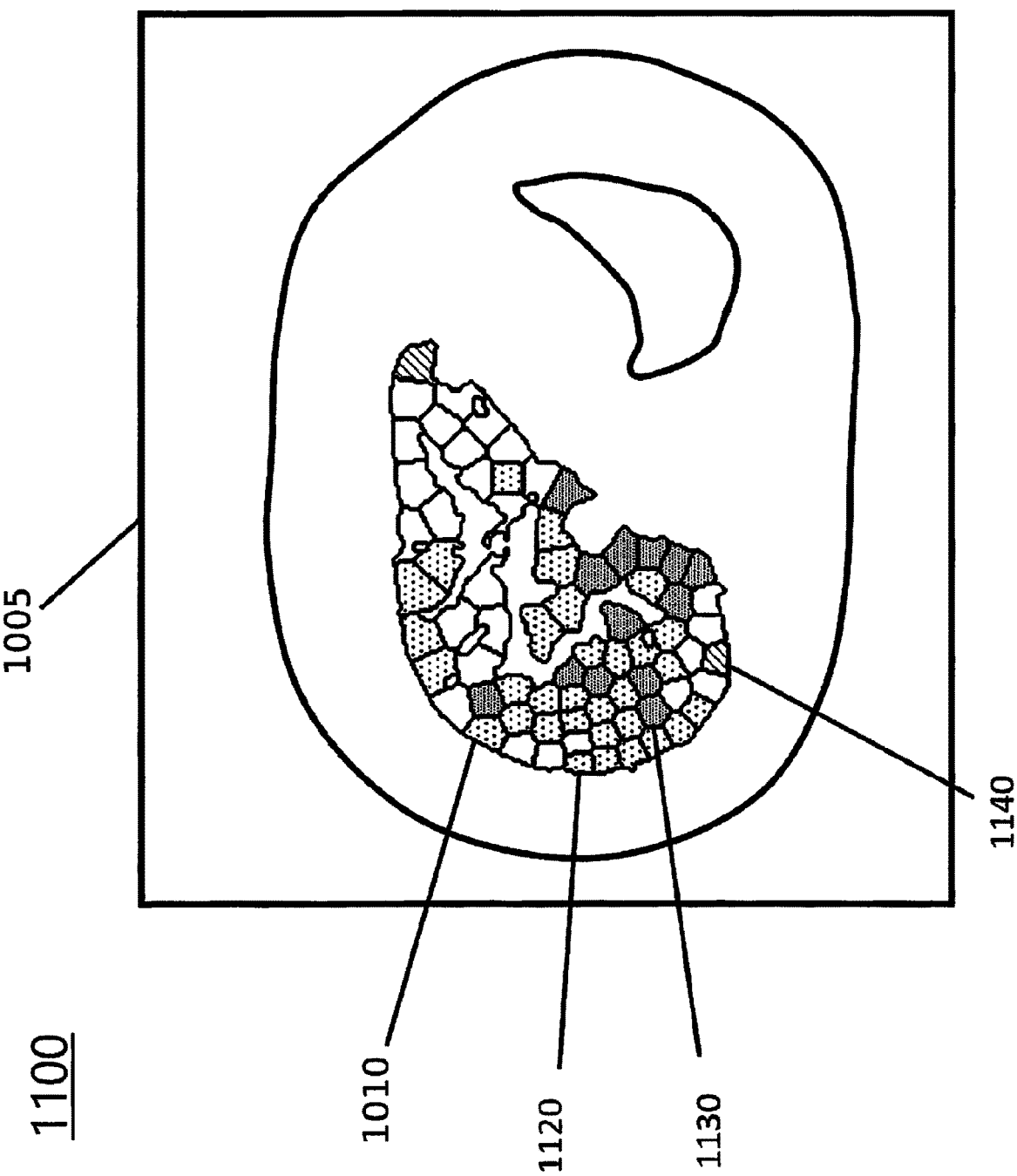
FIG. 11 illustrates the slice of FIG. 109 with cross-hatch overlay.

FIG. 11 illustrates the slice 1005 of FIG. 10 with cross-hatch overlay.

Shown again at 1000 is slice 1005. The examples of subregions that are marked in FIG. 11 are first subregion 1120, second subregion 1130 and third subregion 1140.

First subregion 1120, second subregion 1130 and third subregion 1140 correspond to first subregion 1020, second subregion 1030 and third subregion 1040 of FIG. 10. However, first subregion 1120, second subregion 1130 and third subregion 1140 are now marked with cross-hatching that indicates the band within which the change in the subregion lies. The scale for the cross-hatch marking is shown at the upper left of slice 1005 in FIG. 11. For example, the cross-hatch marking of first subregion 1120 indicates that the change in cT1 value falls in the range of −50 ms to −30 ms.

The plot in FIG. 11 may correspond to the plot described in step 840 of method 800.

Figure 12:
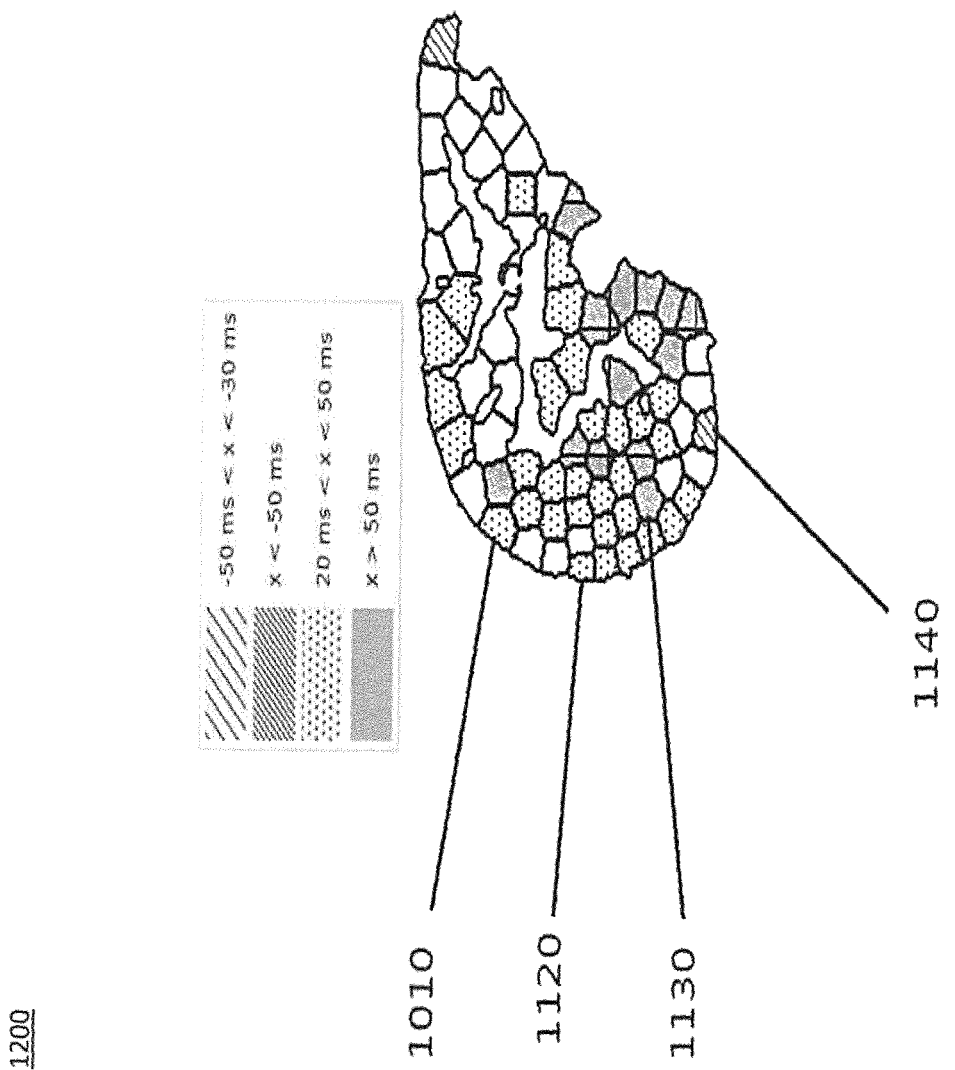
FIG. 12 illustrates the cross-hatch overlay of FIG. 11.

FIG. 12 illustrates the cross-hatch overlay of FIG. 11. Shown again at 1200 is image 1010. Also shown in FIG. 12 are first subregion 1120, second subregion 1130 and third subregion 1140 from FIG. 11. FIG. 12 differs from FIG. 11 in that the parts of medical scan image 100 that lie outside image 1010 have been discarded from the plot, in order to make image 1010 and the subregions within image 1010 stand out more clearly.

Figure 13:
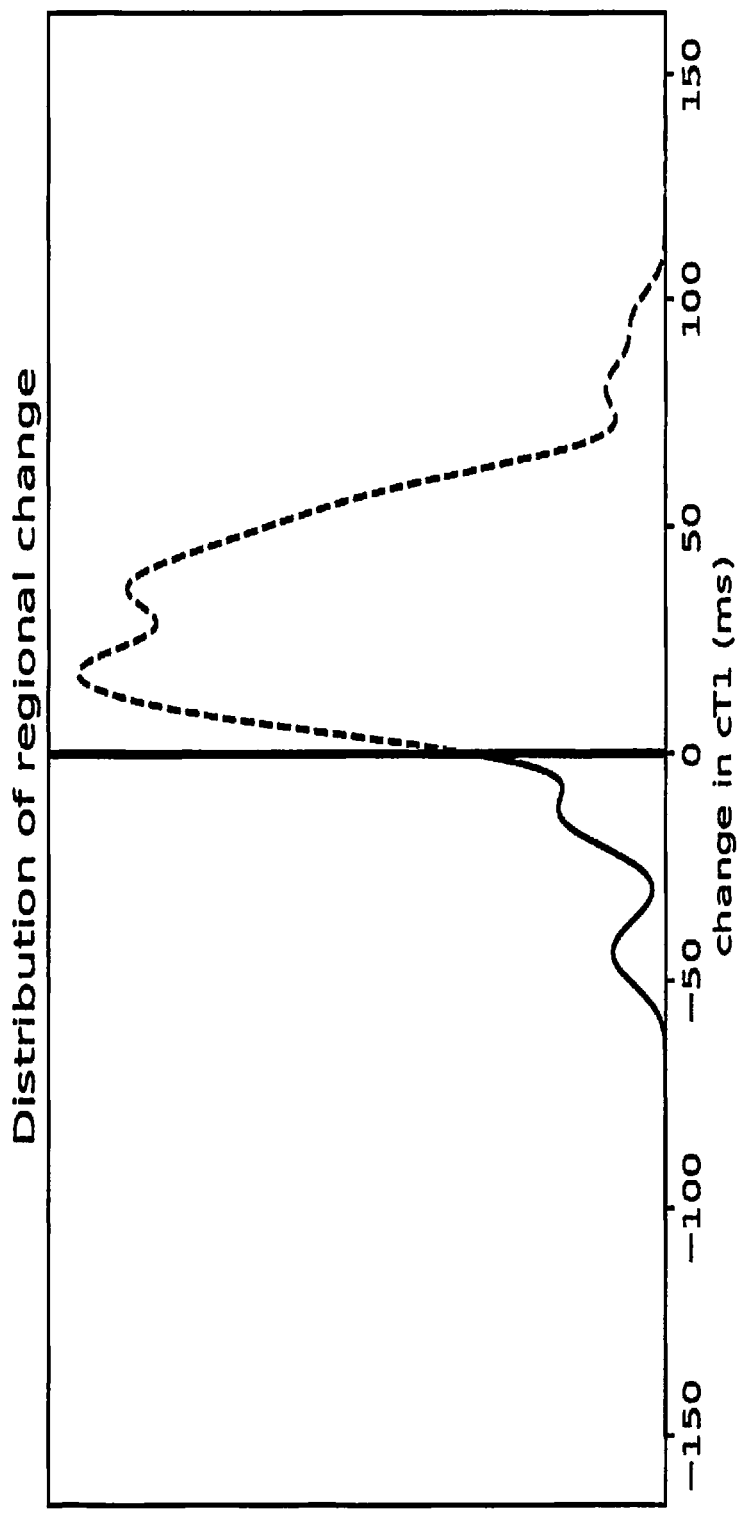
FIG. 13 illustrates a distribution of change across an image of a visceral organ.

FIG. 13 illustrates a distribution of change across an image of a visceral organ.

The distribution of change across an image shown at 1300 in FIG. 13 may be based on a distribution of change across superpixels in the image. In the form used in FIG. 13, the plot has been normalised to have an area of 1 under the curve shown.

In the example plot of FIG. 13, most of the subregions have shown an increase in cT1 value, see the portion of the curve to the right of the vertical axis (the conventional 'y-axis'). However, a small proportion of the subregions has shown a decrease in cT1 value, see the portion of the curve to the left of the vertical axis.

The distribution of change across a medical scan shown in FIG. 13 provides an alternative view of the information derived from any of the methods 600, 700 or 800 described above.

A threshold can be applied to the distribution of change shown in FIG. 13. The threshold would appear as a vertical line at the point on the 'change in cT1 (ms)' axis (the conventional 'x-axis') that corresponded to the value chosen for the threshold.

Figure 14:
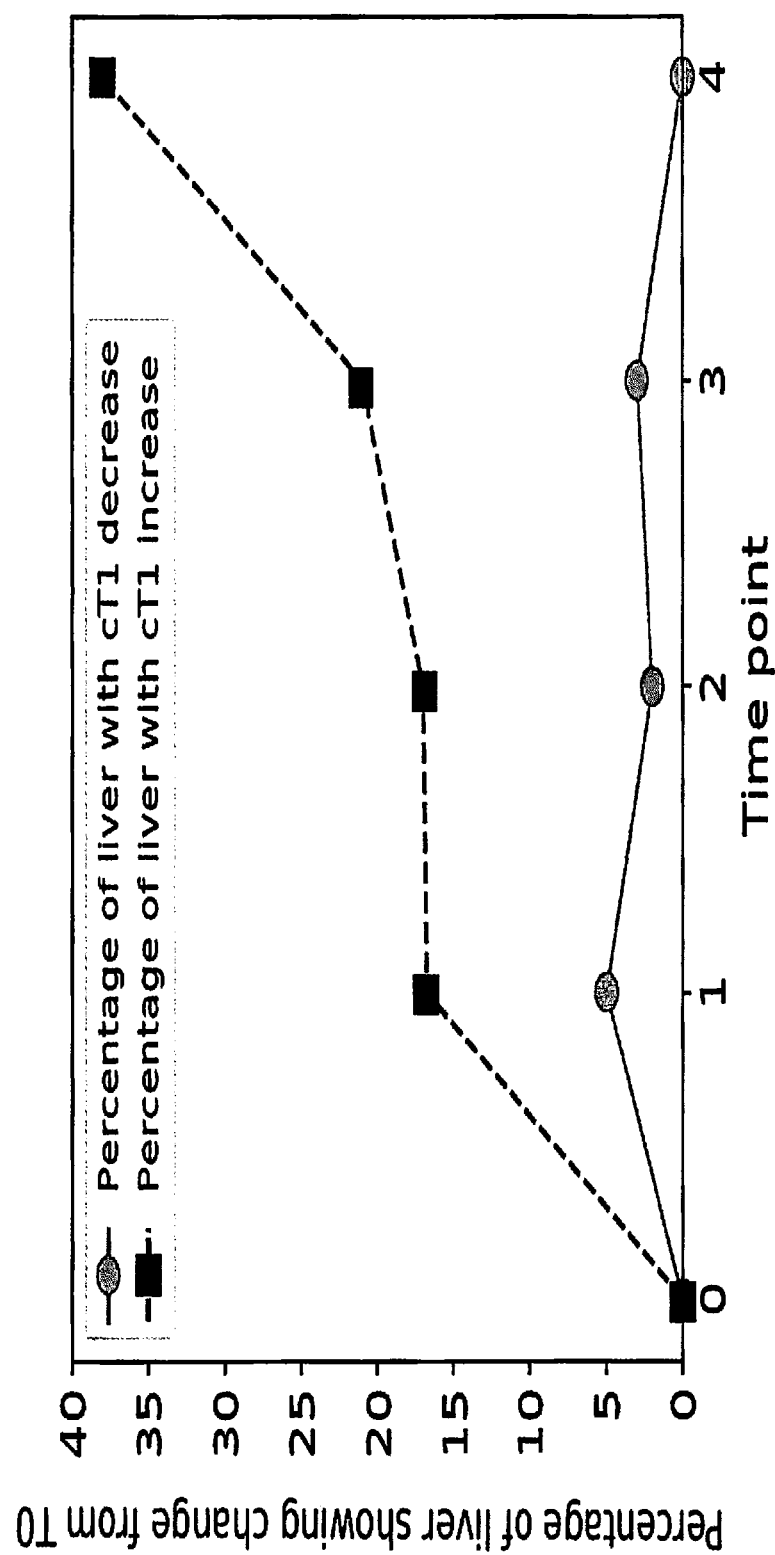
FIG. 14 illustrates a percentage change across five timepoints.

FIG. 14 illustrates a percentage change across five timepoints.

In FIG. 14, the graph 1400 shows timepoints that are marked as 0 to 5 along the horizontal axis. The percentage change from the first medical image onwards is shown on the vertical axis.

The plot denoted with square icons shows the percentage of the visceral organ, here a liver, that has shown an increase in cT1 value that exceeds a first threshold.

The plot denoted with circular icons shows the percentage of the visceral organ that has shown a decrease in cT1 value that exceeds a second threshold. So, for example, at the third scan at timepoint 2, more than 15% of the visceral organ has shown an increase in cT1 value that exceeds the first threshold. However, at the third scan at timepoint 2, only around 2% of the visceral organ has shown a decrease in cT1 value that exceeds the second threshold.

The plots shown in FIG. 14 maybe examples of those described with reference to step 940 in FIG. 9. The percentage values shown on FIG. 14 are percentage results that are of the same general form as the values shown in any row of Table 2 above.

Figure 15:
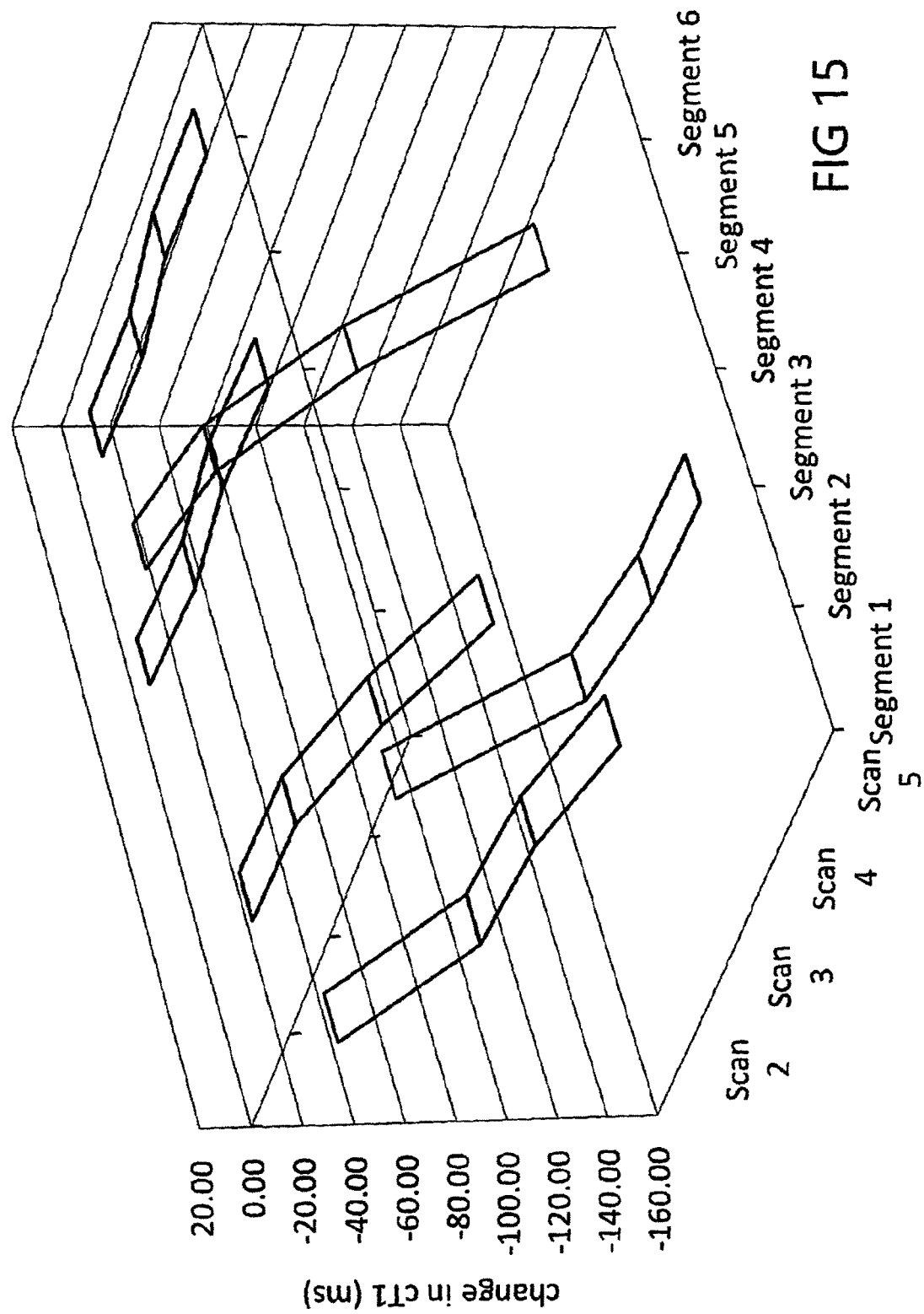
FIG. 15 illustrates the development over time of multiple subregions of a medical image.

FIG. 15 illustrates the development over time of multiple subregions of a medical scan. At 1500, FIG. 15 illustrates an example of a plot showing six subregions. The subregions are labelled as 'Segments' on FIG. 15, along the axis that is conventionally referred to as the 'y-axis' of a 3-D plot. Marked on the axis conventionally referred to as the 'x-axis' of a 3-D plot are the five scans 'Scan 2' ... 'Scan 5' that were performed at different timepoints, after an initial scan to establish baseline cT1 values.

Values of the change in cT1 are shown on the axis conventionally referred to as the 'z-axis' of a 3-D plot. FIG. 15 makes clear, for example, that Segment 3 showed a strong reduction in cT1 value by the time of 'Scan 2'. Segment 5 also showed a strong reduction in cT1 value, but much of that reduction occurred after 'Scan 4'.

Figure 16:
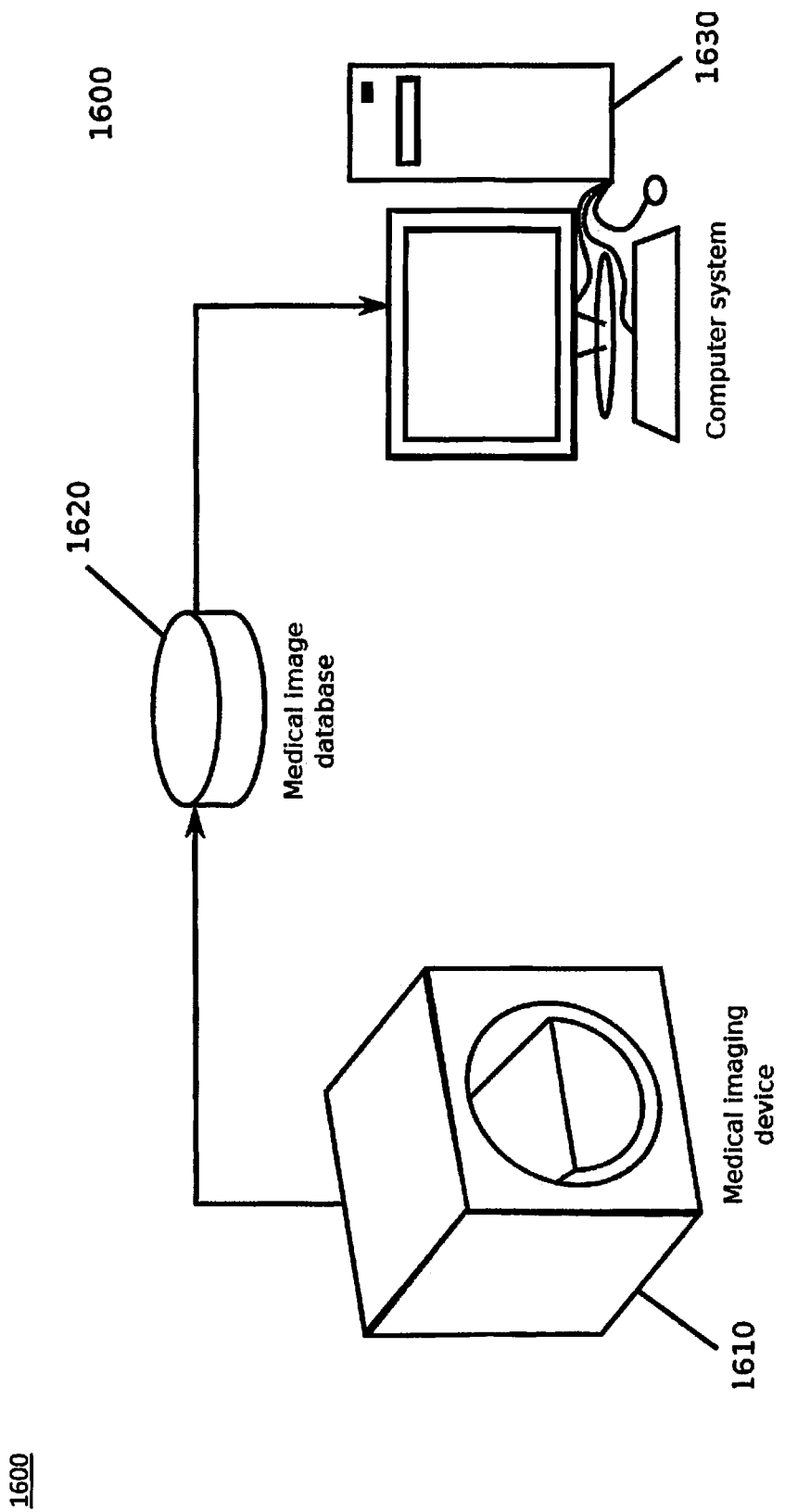
FIG. 16 illustrates a medical scanning system in accordance with the invention.

FIG. 16 illustrates a medical scanning system 1600 in accordance with the invention. FIG. 16 shows a medical imaging device 1610, which may be an MRI scanner. Medical imaging device 1610 is linked to medical image database 1620. In turn, medical image database 1620 is linked to computer system 1630. Together, medical imaging device 1610, medical image database 1620 and computer system 1630 may implement the methods of the invention.

Although FIG. 16 shows medical imaging device 1610, medical image database 1620 and computer system 1630, the invention may be carried out by only some of these elements. For example, the methods of the invention may be applied to scans of various kinds that are held in medical image database 1620. Some of the scans may not originate from medical imaging device 1610, but may originate from other sources. Alternatively, computer system 1630 may apply the methods of the invention to a series of datasets containing medical scans that were not obtained for the purpose of use with the present invention. So the invention may be applied to historical datasets, which were collected for other purposes than the present invention.

Figure 17:
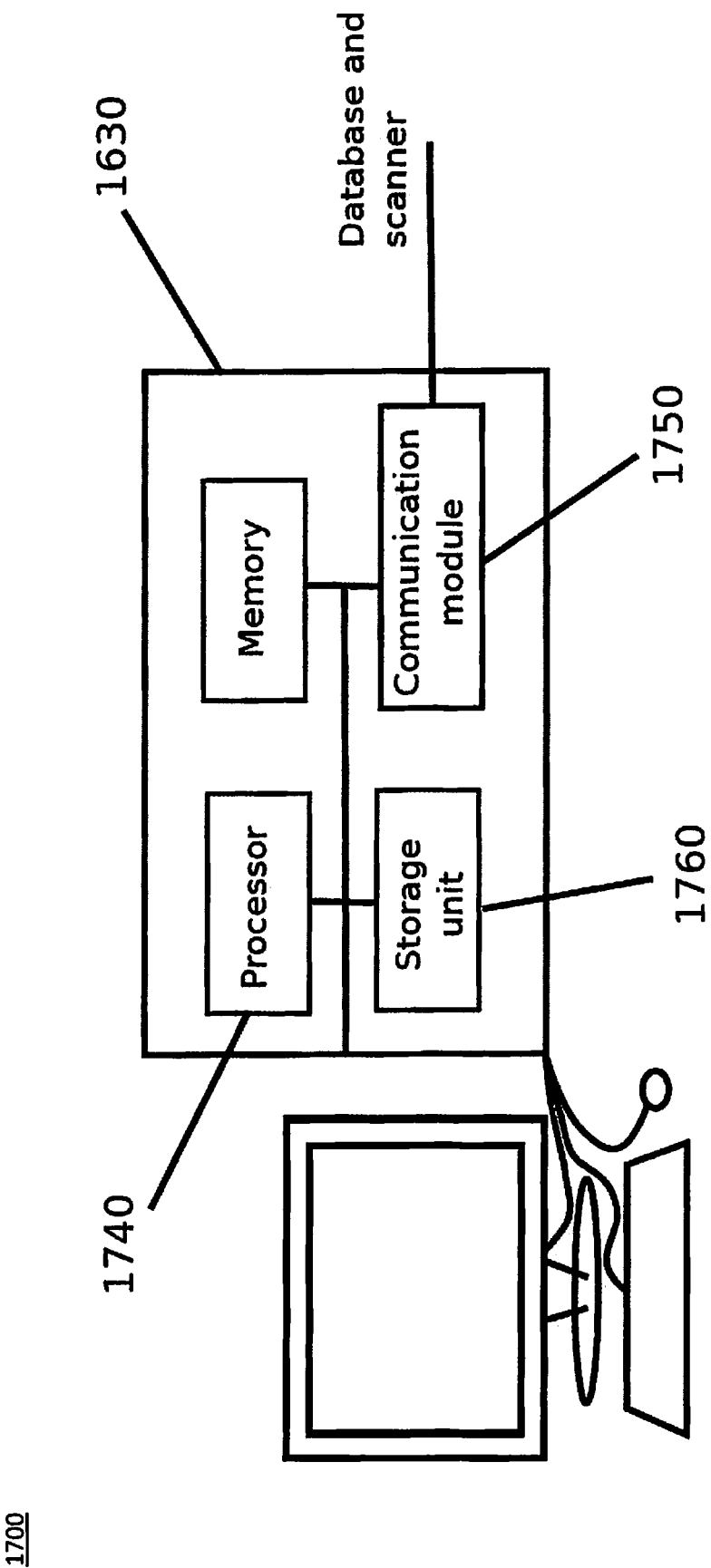
FIG. 17 illustrates details of a medical scanning system in accordance with the invention.

FIG. 17 illustrates details at 1700 of the medical scanning system 1600, in accordance with the invention. Computer system 1630 shown in FIG. 17 corresponds to computer system 1630 shown in FIG. 16. Forming part of computer system 1630 are processor 1740, communication module 1750 and storage unit 1760. Communication module 1750 may link computer system 1630 to medical image database 1620 and medical imaging device 1610 of FIG. 16 and/or other sources of datasets comprising medical scans.

Considering FIGS. 16 and 17, processor 1740 and medical imaging device 1610 may be together configured to provide a medical scanning system in accordance with the third aspect of the invention. Medical imaging device 1610 obtains medical scans of a visceral organ of a human subject at different timepoints. Medical imaging device 1610 is configured to acquire a first medical scan of a human subject at a first timepoint, the first medical scan being part of a first dataset and comprising a first set of voxels, the first medical scan comprising a first image of a visceral organ. The medical imaging device 1610 is also configured to acquire a second medical scan of the human subject at a second timepoint, the second medical scan being part of a second dataset and comprising a second set of voxels, the second medical scan comprising a second image of the visceral organ, and wherein the second timepoint may be before or after the first timepoint.

Processor 1740 is configured to quantify changes in the visceral organ by:
(i) Parcellating at least part of the first image 310 of the visceral organ in the first medical scan into a first set of subregions based on image content. Each subregion of the first set of subregions is defined by a regional representation comprising a plurality of voxels, and is non-overlapping with other subregions of the first set of subregions.
(ii) Aligning the first medical scan and the second medical scan, before or after parcellating the first image 310 of the visceral organ.
(iii) Parcellating at least part of the second image 410 of the visceral organ into a second set of subregions. Each subregion of the second set of subregions is defined by a regional representation comprising a plurality of voxels of the second set of voxels, and is non-overlapping with other subregions of the second set of subregions. Parcellating at least part of the second image 410 of the visceral organ is based on the first set of subregions.
(iv) Evaluating a metric for a subregion in the first image 310 of the visceral organ to provide a first value of the metric, and evaluating the metric for a corresponding subregion in the second image 410 of the visceral organ to provide a second value of the metric.
(v) Evaluating a difference between the first value of the metric and the second value of the metric, thereby providing a measure of a change that has occurred in the subregion between the first timepoint and the second timepoint.

Although the medical scanning system 1600 described above is configured to implement the method of the first aspect of the invention, the processor 1740 of medical scanning system 1600 can additionally or instead be configured to implement the method of the second aspect of the invention as specified in appended claim 2.

In accordance with the fourth aspect of the invention, a non-transitory computer program product is provided. The non-transitory computer program product has executable program code stored therein, the program code operable for quantifying changes in a visceral organ in accordance with any of the methods described above.

The non-transitory computer program product comprises at least one from a group including: a hard disk, a CD-ROM, an optical storage device, a magnetic storage device, a Read Only Memory, ROM, a Programmable Read Only Memory, PROM, an Erasable Programmable Read Only Memory, EPROM, an Electrically Erasable Programmable Read Only Memory, EEPROM, and a Flash memory.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources.

An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims. Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

The invention claimed is:

1. A method of quantifying changes in a visceral organ of a human subject, the method comprising:
    acquiring a first medical MRI scan at a first timepoint, the first medical scan being part of a first dataset and comprising a first set of voxels, the first medical scan comprising a first image of a visceral organ;
    acquiring a second medical MRI scan at a second timepoint, the second medical scan being part of a second dataset and comprising a second set of voxels, the second medical scan comprising a second image of the visceral organ, and wherein the second timepoint may be before or after the first timepoint;
    whereby each voxel in the first and second set of voxels provides either quantitative T1 values, quantitative T2*values, cT1 values that are based on T1 values using T2* as a correction, or PDFF values; or a combination of T1, T2* and/or PDFF values;
    parcellating at least part of the first image of the visceral organ into a first set of subregions based on image content, each subregion of the first set of subregions being defined by a regional representation comprising a plurality of voxels of the first set of voxels, and being non-overlapping with other subregions of the first set of subregions;
    aligning the first medical scan and the second medical scan, before or after parcellating the first image of the visceral organ;
    parcellating at least part of the second image of the visceral organ into a second set of subregions, each subregion of the second set of subregions being defined by a regional representation comprising a plurality of voxels of the second set of voxels, and being non-overlapping with other subregions of the second set of subregions;
    wherein parcellating at least part of the second image of the visceral organ is based on the first set of subregions;
    evaluating a metric for a subregion in the first image of the visceral organ to provide a first value of the metric, and evaluating the metric for a corresponding subregion in the second image of the visceral organ to provide a second value of the metric; and
    evaluating a difference between the first value of the metric and the second value of the metric, being a difference for the subregion in either: the T1 values, the T2* values, the cT1 values, or the PDFF values;
    thereby providing a measure of a change that has occurred in the subregion between the first timepoint and the second timepoint.

2. A method of quantifying changes in a visceral organ of a human subject, the method comprising:
    acquiring a first medical MRI scan at a first timepoint, the first medical scan being part of a first dataset and comprising a first set of voxels, the first medical scan comprising a first image of a visceral organ;
    acquiring a second medical MRI scan at a second timepoint, the second medical scan being part of a second dataset and comprising a second set of voxels, the second medical scan comprising a second image of the visceral organ;
    whereby each voxel in the first and second sets of voxels provides either:
    quantitative T1 values, quantitative T2*values, cT1 values that are based on T1 values using T2* as a correction, or PDFF values; or a combination of T1, T2* and/or PDFF values;
    aligning the first medical scan and the second medical scan, and then parcellating the first image of the visceral organ and the second image of the visceral organ jointly, based on image content for at least part of the first image of the visceral organ and the second image of the visceral organ;
    whereby:
    parcellating the first image of the visceral organ provides a first set of subregions, each subregion of the first set of subregions being defined by a first regional representation comprising a plurality of voxels, and being non-overlapping with other subregions of the first set of subregions;

parcellating the second image of the visceral organ provides a second set of subregions, each subregion of the second set of subregions being defined by a second regional representation comprising a plurality of voxels, and being non-overlapping with other subregions of the second set of subregions; and the first set of subregions and the second set of subregions correspond;

evaluating a metric for a subregion in the first image of the visceral organ to provide a first value of the metric, and evaluating the metric for a corresponding subregion in the second image of the visceral organ to provide a second value of the metric;

evaluating a difference between the first value of the metric and the second value of the metric, being a difference for the subregion in either: the T1 values, the T2* values, the cT1 values, or the PDFF values thereby providing a measure of a change that has occurred in the subregion between the first timepoint and the second timepoint.

3. The method of quantifying changes in a visceral organ of a human subject as in claim 1, wherein:
the first dataset is one of a 3D volumetric image, a stack of 2D image slices or a single 2D image slice; and
the second dataset is one of a 3D volumetric image, a stack of 2D image slices or a single 2D image slice.

4. The method of quantifying changes in a visceral organ of a human subject as in claim 1:
wherein the first medical scan is a first slice from the first dataset, and the second medical scan is a second slice from the second dataset; and
and further comprising:
deriving the first image of the visceral organ by segmenting parts of the first slice that show the visceral organ from other parts of the first slice; and
deriving the second medical scan of the visceral organ by segmenting parts of the second slice that show the visceral organ from other parts of the second slice.

5. The method of quantifying changes in a visceral organ of a human subject as in claim 1, wherein parcellating at least part of the visceral organ, based on the image content, comprises:
parcellating based on intensities of the first set of voxels and/or intensities of the second set of voxels.

6. The method of quantifying changes in a visceral organ of a human subject as in claim 1, wherein parcellating the first image of the visceral organ and/or the second image of the visceral organ:
creating a piece-wise constant representation of the visceral organ, whereby each subregion is locally similar.

7. The method of quantifying changes in a visceral organ of a human subject as in claim 4, wherein parcellating the first image of the visceral organ and/or the second image of the visceral organ further comprises superpixel clustering within the visceral organ, after the segmenting.

8. The method of quantifying changes in a visceral organ of a human subject as in claim 1, wherein parcellating the first image of the visceral organ and/or the second image of the visceral organ further comprises creating a representation of local similarity within the visceral organ, wherein similarity is defined on the basis of either: multiple imaging modalities; or texture.

9. The method of quantifying changes in a visceral organ of a human subject as in claim 1, wherein the step of aligning comprises either:
aligning image content-derived information that defines the first medical scan and the second medical scan;
aligning image content-derived information that defines first image of the visceral organ and the second image of the visceral organ; or
using a transformation to explicitly align:
points that lie on boundaries of subregion(s); and/or
points that lie on a boundary of the visceral organ.

10. The method of quantifying changes in a visceral organ of a human subject as in claim 1, wherein the first time point and the second time point are separated by sufficient time for the visceral organ to have undergone either a change in shape, or a change in the characteristics of at least one subregion.

11. The method of quantifying changes in a visceral organ of a human subject as in claim 1, wherein the metric is a summary statistic of spatial texture across at least one subregion.

12. The method of quantifying changes in a visceral organ of a human subject as in claim 1, further comprising:
evaluating the metric for a plurality of subregions of the first image of the visceral organ and for corresponding subregions of the second image of the visceral organ;
evaluating the difference between the first value of the metric and the second value of the metric for each subregion, to thereby provide a plurality of difference values; and
plotting the plurality of difference values on either a graph or on a spatial plot of the subregions, whereby the graph or spatial plot provides a visual projection of changes in each subregion between the first timepoint and the second timepoint.

13. The method of quantifying changes in a visceral organ of a human subject as in claim 12, further comprising:
acquiring a third medical scan of the visceral organ at a third timepoint, the third medical scan comprising a third image of a visceral organ;
repeating the method steps of claim 1 or claim 2 for the third medical scan and at least one of the first medical scan and the second medical scan; and
plotting difference values for the metric between the first, second and third images of the visceral organ, either on a graph or on a spatial plot, to provide a visual projection of changes that have occurred in subregions between the first, second and third timepoints.

14. The method of quantifying changes in a visceral organ of a human subject as in claim 1, further comprising:
defining a threshold of change;
comparing the difference between the first value of the metric and the second value of the metric against the threshold of change for at least one subregion, thereby identifying whether the threshold of change has been exceeded for the at least one subregion; and
displaying the first medical scan or the second medical scan with an overlay showing subregions for which the metric has exceeded the threshold of change.

15. The method of quantifying changes in a visceral organ of a human subject as in claim 14, further comprising:
calculating a percentage of the visceral organ that has undergone a change that exceeds the threshold of change.

16. The method of quantifying changes in a visceral organ of a human subject as in claim 13, further comprising:
defining a threshold of change;
comparing differences between the first, second and third values of the metric against the threshold of change for the subregions, thereby identifying whether the threshold of change has been exceeded for the subregions;

calculating a percentage of the visceral organ that has undergone a change that exceeds the threshold of change, for the second and/or third medical scans; and plotting the percentages of the visceral organ that have undergone the change that exceeds the threshold of change for the second and/or third medical scans.

17. A method of quantifying changes in a visceral organ of a human subject as in claim 1, wherein the method uses a non-transitory computer program product having executable program code stored therein, the program code operable for quantifying changes in a visceral organ.

18. A method of quantifying changes in a visceral organ of a human subject as in claim 17, wherein the non-transitory computer program product comprises at least one from a group including: a hard disk, a CD-ROM, an optical storage device, a magnetic storage device, a Read Only Memory, ROM, a Programmable Read Only Memory, PROM, an Erasable Programmable Read Only Memory, EPROM, an Electrically Erasable Programmable Read Only Memory, EEPROM, and a Flash memory.

19. A medical scanning system comprising:
a medical MRI imaging device, the medical imaging device configured to:
acquire a first medical scan of a human subject at a first timepoint, the first medical scan being part of a first dataset and comprising a first set of voxels, the first medical scan comprising a first image of a visceral organ;
acquire a second medical scan of the human subject at a second timepoint, the second medical scan being part of a second dataset and comprising a second set of voxels, the second medical scan comprising a second image of the visceral organ, and wherein the second timepoint may be before or after the first timepoint;
whereby each voxel in the first and second sets of voxels provides either:
quantitative T1 values, quantitative T2* values, cT1 values, that are based on T1 values using T2* as a correction, or PDFF values, or a combination of T1, T2* and/or PDFF values, and a processor, the processor configured to quantify changes in the visceral organ by:
parcellating at least part of the first image of the visceral organ into a first set of subregions based on image content, each subregion of the first set of subregions being defined by a regional representation comprising a plurality of voxels, and being non-overlapping with other subregions of the first set of subregions;
aligning the first medical scan and the second medical scan, before or after parcellating the first image of the visceral organ;
parcellating at least part of the second image of the visceral organ into a second set of subregions, each subregion of the second set of subregions being defined by a regional representation comprising a plurality of voxels of the second set of voxels, and being non-overlapping with other subregions of the second set of subregions;
wherein parcellating at least part of the second image of the visceral is based on the first set of subregions;
evaluating a metric for a subregion in the first image of the visceral organ to provide a first value of the metric, and evaluating the metric for a corresponding subregion in the second image of the visceral organ to provide a second value of the metric; and
evaluating a difference between the first value of the metric and the second value of the metric, being a difference for the subregion in either: the T1 values, the T2* values, the cT1 values, or the PDFF values thereby providing a measure of a change that has occurred in the subregion between the first timepoint and the second timepoint.

* * * * *